(12) United States Patent
Elledge et al.

(10) Patent No.: US 7,338,800 B2
(45) Date of Patent: Mar. 4, 2008

(54) IN VIVO GENE TRANSFER

(75) Inventors: Stephen J. Elledge, Houston, TX (US); Mamie Z. Li, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 468 days.

(21) Appl. No.: 10/345,523

(22) Filed: Jan. 16, 2003

(65) Prior Publication Data

US 2003/0224481 A1    Dec. 4, 2003

Related U.S. Application Data

(60) Provisional application No. 60/350,182, filed on Jan. 16, 2002.

(51) Int. Cl.
C12N 15/74     (2006.01)
C12N 15/00     (2006.01)
C12N 1/20      (2006.01)

(52) U.S. Cl. .................. 435/471; 435/320.1; 435/252.3

(58) Field of Classification Search ............... None
See application file for complete search history.

(56) References Cited

U.S. PATENT DOCUMENTS

| | | | |
|---|---|---|---|
| 5,851,808 A | 12/1998 | Elledge et al. | |
| 6,162,966 A * | 12/2000 | Kossmann et al. | 800/284 |
| 6,270,969 B1 | 8/2001 | Hartley et al. | |
| 6,277,608 B1 | 8/2001 | Hartley et al. | |
| 6,355,412 B1 | 3/2002 | Stewart et al. | |
| 6,376,192 B1 | 4/2002 | Elledge et al. | |
| 6,509,156 B1 | 1/2003 | Stewart et al. | |
| 2002/0102734 A1 * | 8/2002 | Menzel | 435/475 |

OTHER PUBLICATIONS

Metcalf et al Gene 138:1-7, 1994.*
Dreiseikelmann, Microbiol. Rev., 58, 3, p. 293-316, 1994.*

Oliner, Jonathan, et al.; In vivo cloning of PCR products in E.Col; Nucleic Acids Research; 1993, vol. 21, No. 22, 5192-5197.
Bubeck, Peter, et al.; Rapid cloning by homologous recombination in vivo. Nucleic Acids Research, 1993, vol. 21, No. 15, 3601-3602.
Nussabaum, A. et al.; Restriction-Stimulated Homologous Recombination of Plasmids by the RecE Pathway of *Escherichia coli*; Jan. 1992, Genetics, vol. 130, 37-49.
Smith, Gerald R.; Conjugational Recombination in E. Col: Myths and Mechanisms; (Jan. 1991) Cell, vol. 64, 19-27.
P. Zhang et al., *Towards genetic genome projects: genomic library screening and gene-targeting . . .* ; Nature Genetics, Jan. 2002, pp. 31-39, vol. 30, 2002 Nature Publishing Group.
*An Introduction to GATEWAY™ Cloning Technology*, Focus (2001) vol. 23, pp. 4-5, Life Technologies, a Div. Of Invitrogen Corp., Rockville, MD.
*Gateway Cloning Technology*, www.invitrogen.com/orphans/gateway05.html, pp. 1-2, printed Jan. 14, 2002.
Q. Liu et al., *The univector plasmid-fusion system, a method for rapid construction. . .* ;Current Biology 1998 pp. 1300-1308, vol. 8, Current Biology Ltd.
*PcDNA6-E© Echo™-Adapted Expression Vector . . .* , Catalog Nos. ET406-XX, pp. I-x and 1-24, Invitrogen Corp., 2000-2001.
*The Echo™ Closing System: The future of cloning is here*, Invitrogen Life Technologies, www.invitrogen.com/content.cfm?pageid=3371&cfid=1425151&cftoken=65400194, printed Jan. 14, 2002, pp. 1-10.

* cited by examiner

*Primary Examiner*—Nancy Vogel
(74) *Attorney, Agent, or Firm*—Fulbright & Jaworski LLP

(57) ABSTRACT

The present invention is directed to an in vivo method of transferring DNA from a donor cell to a recipient cell. In a specific embodiment, the method comprises a highly efficient process of bacterial mating. In a preferred embodiment, selection for a recombinant plasmid against a parent host plasmid and donor plasmid is based on recircularization of the host plasmid by its recombination with a gene of interest such that it is now no longer cleaved by a restriction enzyme expressed in the recipient cell.

30 Claims, 16 Drawing Sheets

FIG. 6

Strain B

These experiments were performed without counter-selection against pheS

These experiments were performed without counter-selection against pheS

SEQUENCE LISTING

```
<160> NUMBER OF SEQ ID NOS: 21

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (4)..(8)
<223> OTHER INFORMATION: N = a, c, g or t/u

<400> SEQUENCE: 1
gacnnnnngt c                                                          11
```

```
<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(13)
<223> OTHER INFORMATION: N = a, c, g, or t/u
<220> FEATURE:
<221> NAME/KEY: modified_base
<222> LOCATION: (11)
<223> OTHER INFORMATION: Y = c or t

<400> SEQUENCE: 2
nacnnnngta ycn                                                          13

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (4)..(9)
<223> OTHER INFORMATION: N = a, c, g or t/u

<400> SEQUENCE: 3
cgannnnnnt gc                                                           12

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (4)..(8)
<223> OTHER INFORMATION: N = a, c, g or t/u

<400> SEQUENCE: 4
gccnnnnngg c                                                            11

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (4)..(7)
<223> OTHER INFORMATION: N = a, c, g or t/u

<400> SEQUENCE: 5 gatnnnnatc                                                              10

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
       Primer
<220> FEATURE:
<221> NAME/KEY: modified_base
<222> LOCATION: (3)..(9)
<223> OTHER INFORMATION: N = a, c, g or t/u

<400> SEQUENCE: 6
ccnnnnnnng g                                                               11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(8)
<223> OTHER INFORMATION: N = a, c, g or t/u

<400> SEQUENCE: 7
gcannnnntg c                                                               11

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(9)
<223> OTHER INFORMATION: N = a, c, g or t/u

<400> SEQUENCE: 8
ccannnnnnt gg                                                              12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(9)
<223> OTHER INFORMATION: N = a, c, g or t/u

<400> SEQUENCE: 9
gacnnnnnng tc                                                              12

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(8)
<223> OTHER INFORMATION: N = a, c, g or t/u

<400> SEQUENCE: 10
cctnnnnnag g                                                               11
```

-continued

```
<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (6)..(9)
<223> OTHER INFORMATION: N = a, c, g or t/u

<400> SEQUENCE: 11 cccgcnnnn                                                                  9

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tagggataac agggtaat                                                       18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
attaccctgt tatcccta                                                       18

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (6)..(10)
<223> OTHER INFORMATION: N = a, c, g or t/u

<400> SEQUENCE: 14 gagtcnnnnn                                                                10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (3)
<223> OTHER INFORMATION: Y = c or t
<220> FEATURE:
<221> NAME/KEY: modified_base
<222> LOCATION: (4)..(7)
<223> OTHER INFORMATION: N = a, c, g or t/u
<220> FEATURE:
<221> NAME/KEY: modified_base
<222> LOCATION: (8)
<223> OTHER INFORMATION: R = a or g
```

```
<400> SEQUENCE: 15 caynnnnrtg                                                          10

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (3)..(9)
<223> OTHER INFORMATION: N = a, c, g or t/u

<400> SEQUENCE: 16
gcnnnnnnng c                                                        11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(8)
<223> OTHER INFORMATION: N = a, c, g or t/u

<400> SEQUENCE: 17
ccannnnntg g                                                        11

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(7)
<223> OTHER INFORMATION: N = a, c, g or t/u

<400> SEQUENCE: 18 gacnnnngtc                                                          10

<210> SEQ ID NO 19
<211> LENGTH: 13
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (5)..(9)
<223> OTHER INFORMATION: N = a, c, g or t/u

<400> SEQUENCE: 19
ggccnnnnng gcc                                                      13

<210> SEQ ID NO 20
<211> LENGTH: 15
<212> TYPE: DNA
<213> ORGANISM: Artificial Sequence
<220> FEATURE:
```

```
-continued

<223> OTHER INFORMATION: Description of Artificial Sequence:  Synthetic
      Primer
<220> FEATURE:
<221> NAME/KEY: modified_base
<222> LOCATION: (4)..(12)
<223> OTHER INFORMATION: N = a, c, g or t/u

<400> SEQUENCE: 20
ccannnnnnn nntgg                                                       15

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)..(7)
<223> OTHER INFORMATION: N = a, c, g or t/u

<400> SEQUENCE: 21 gaannnnttc                                                             10
```

IN VIVO GENE TRANSFER

This application claims priority to U.S. Provisional Patent Application Ser. No. 60/350,182, filed Jan. 16, 2002, incorporated by reference herein in its entirety.

FIELD OF THE PRESENT INVENTION

The present invention is directed to the fields of molecular biology, cloning, and bacterial genetics. More specifically, the present invention addresses an in vivo transfer of DNA from one clone to another via bacterial conjugation and homologous recombination.

BACKGROUND OF THE INVENTION

Current molecular biology practices require a significant amount of DNA cloning to provide necessary research tools. The motivation for developing a new system of precise gene transfer to generate these tools stems from separate factors. The first is that current methods regard in vitro manipulations that require undesirable quantities of DNA purification. For example, the ability to transfer a polynucleotide of interest to an expression vector is often limited by the availability or suitability of restriction enzyme recognition sites. Often, multiple restriction enzymes must be employed for the removal of the polynucleotide of interest, and the reaction conditions used for each enzyme may differ such that it is necessary to perform the excision reactions in separate steps. In addition, it may be necessary to remove a particular enzyme used in an initial restriction enzyme reaction prior to completing all restriction enzyme digestions, which requires a time-consuming purification of the subcloning intermediate. Ideal methods for the subcloning of DNA molecules would permit the rapid transfer of the target DNA molecule from one vector to another, preferably in vivo, without the need to rely upon restriction enzyme digestion(s). Furthermore, the larger the gene set, the greater the additional effort that is required.

Given that the need to manipulate large numbers of DNAs requires robotics that are frequently beyond the abilities of most small labs, a simpler way to transfer genes between different vectors, allowing smaller labs to efficiently study entire genomes at greatly reduced expense, is desirable.

U.S. Pat. No. 5,851,808 and Liu et al. (1998) are directed to the Echo™ Cloning system (also referred to as the Univector Plasmid Fusion System) (Invitrogen; Carlsbad, Calif.) that comprises a vector (pUNI) into which sequences encoding a gene of interest are inserted. The pUNI vector has a single sequence-specific recombinase target site, in specific embodiments a loxP site, preceding the insertion site for the gene of interest, a selectable marker gene and a conditional origin of replication that is active only in host cells expressing the requisite trans-acting replication factor. The pUNI vectors are designed to contain a gene of interest but lack a promoter for the expression of the gene of interest. Using a sequence-specific recombinase (e.g., Cre recombinase), a precise fusion of the pUNI vector into a second vector containing another copy of the sequence-specific recombinase target site as on the pUNI vector occurs. The second vector, referred to generically as a pHOST vector (or pAcceptor vector), is an expression vector that contains the sequence-specific recombinase target site downstream of the promoter element contained within the expression vector. Following the site-specific recombination event that occurs between the single sequence-specific recombinase target sites located on each vector (e.g., the pUNI vector and the pHOST vector), the two vectors are stably fused in a manner that places the expression of the gene of interest under the control of the promoter element contained within the expression vector. This fusion event also occurs in a manner that retains the proper translational reading frame of the gene of interest. This subcloning event occurs without the need to use restriction enzymes. The fusion or recombination event can be selected for by selecting for the ability of host cells, which do not express the trans-acting replication factor required for replication of the conditional origin contained on the pUNI vector, to acquire the selectable phenotype conferred by the selectable marker gene (if present) on the pUNI vector. The pUNI vector cannot replicate in cells lacking expression of the trans-acting replication factor and therefore, unless the pUNI vector has integrated into the second vector that contains a non-conditional origin of replication, pUNI will be lost from the host cell.

In technology similar to the Echo system, the site-specific recombination system of phage lambda, GATEWAY™ Cloning Technology (Invitrogen; Carlsbad, Calif.) (U.S. Pat. No. 6,277,608), allows transfer of DNA segments between different cloning vectors while maintaining orientation and reading frame, also effectively replacing the use of restriction endonucleases and ligase. Homologous recombination is not utilized. The phage lambda system utilizes the integration sites attB/attP. In specific embodiments, the method for cloning or subcloning desired nucleic acid molecules comprises a first step of combining in vitro or in vivo (1) one or more insert donor molecules comprising one or more nucleic acid segments flanked by two or more recombination sites, wherein the recombination sites do not substantially recombine with each other; (2) two or more different vector donor molecules, each comprising two or more recombination sites, wherein the recombination sites do not substantially recombine with each other; and (3) one or more site specific recombination proteins; and a second step of incubating the combination under conditions sufficient to transfer one or more of the nucleic acid segments into the different vector donor molecules, thereby producing two or more different product molecules.

U.S. Pat. No. 6,270,969 describes an in vitro method for apposing an expression signal and a gene or partial gene comprising (a) mixing in vitro a first nucleic acid molecule comprising an expression signal and at least a first recombination site, and a second nucleic acid molecule comprising a gene or partial gene and at least a second recombination site; and (b) incubating the mixture in vitro in the presence of at least one recombination protein under conditions sufficient to cause recombination of at least the first and second recombination sites, thereby apposing the expression signal and the gene or partial gene such that expression of the gene or partial gene can be controlled by the expression signal.

Zhang et al. (2002) describes methods for recombination cloning that facilitate genomic library construction and screening. The technology is particularly useful for preparing gene-targeting constructs, such as for targeted gene disruption in mouse embryonic stem cells. Although multiple embodiments are addressed, a specific embodiment regarding utilization of targeting fragments generated in cells that are induced to express I-SceI and are simultaneously infected with library phage is described. The fragment that contains an antibiotic resistance marker for selection is released by digestion of the vector with I-SceI and then recombines with phage DNA carrying the proper homology. The amplified phage are collected and used to infect a cre-expression strain for automatic subcloning; these cells are then subjected to selection for identification of homologous recombinants. Survival occurs only for those cells having plasmids that have undergone recombination.

Despite these technologies available to a skilled artisan, there still remains the need for an in vivo method that does not require the need for DNA preparation of donor clones, is affordable even to small labs, provides flexibility for adaptor sequences, is compatible with other systems, and/or is less laborious than available methods. The present invention addresses these needs.

SUMMARY OF THE INVENTION

The present invention is directed to a method for transferring a polynucleotide of interest into a vector. In specific embodiments, the transfer is from one clone to another.

The present invention is dissimilar to other methods in the art, given that, at the very least, the present invention does not comprise substantially complete integration of two separate vectors together to form a third vector utilizing single recombination sites on the two separate vectors, described in U.S. Pat. Nos. 5,851,808 and 6,270,969. The present invention is also novel given that it utilizes homologous recombination and does not require utilization of a sequence-specific recombinase. The present invention, in specific embodiments, comprises one donor molecule comprising two homologous recombination sites, preferably lacking the ability to recombine with each other. In embodiments of the present invention, the donor molecule is a PCR fragment, a restriction fragment, or a vector. In further embodiments, the donor molecule comprising the two homologous recombination sites recombines with two corresponding sites on a recipient polynucleotide, such as a recipient vector. In specific embodiments, the homologous recombination is preceded by a double strand break of the recipient vector and/or a double strand break of the donor vector. In specific embodiments, the double strand break comprises digestion with an endonuclease, such as a restriction endonuclease.

Thus, in one embodiment of the present invention, a polynucleotide of interest comprising first and second homology regions is transferred by homologous recombination into a vector comprising the first and second homology regions under suitable conditions in vivo, such as in an *E. coli* bacteria.

In one embodiment of the present invention, the transfer of DNA from a donor clone to a recipient clone is performed in vivo by the highly efficient process of bacterial mating. Thus, the donor vector comprising the polynucleotide of interest is transferred to the cell comprising the recipient or host vector. The donor vector is incapable of replicating in the strain harboring the host vector.

In another embodiment of the present invention, this method is directed to the transfer of the gene of interest to the host vector in a precise fashion that maintains both orientation and reading frame. This is accomplished by homologous recombination that is initiated by double strand breaks introduced into both the donor vector and the host vector, in preferred embodiments. These breaks are designed to reveal approximately 50 base pairs (or less) of homology that serve to align and reassemble an intact circular plasmid. However, a skilled artisan recognizes that in some embodiments the donor may not absolutely need to have at least one rare restriction enzyme site or the recipient may not need one (or more). In specific embodiments, it is sufficient if only one of them has such site(s). In a specific example, the recipient will need them in the case where the donor lacks them. However, in further specific embodiments, if the recipient lacks the site(s), then the donor will probably also need to have a selectable marker associated with it.

In an additional embodiment of the present invention, there is the selection for gene transfer, which selects for the recombinant plasmid and against the parent host plasmid and the donor strain. This is accomplished in at least one of several ways. In one version of the system, a drug marker is linked to the gene of interest, and its transfer is selected in the background of the host strain. However, in a preferred version of the system, the selection is based on the recircularization of the host plasmid by its recombination with the gene of interest from the donor plasmid such that it is now no longer cleaved by the restriction enzyme expressed in the recipient cell. Homologous recombinants form molecules that lack the restriction sites. Secondly, the host plasmid comprises a negative selectable marker that is replaced in the recombinant molecule, thereby providing another important layer of selection.

The efficiency of this system is very high. In the version in which a drug marker is linked to the gene of interest, the efficiency is close to 100%. In the version without the drug, the efficiency was measured as 99.8% correct recombinants. Furthermore, a skilled artisan is aware that various fine tuning genetic aspects could conceivably improve upon this efficiency, although the current system is sufficiently robust to use in its current form.

A skilled artisan recognizes there are numerous advantages of this system over other methods. For example, the method is significantly simpler than other methods in the art. It is all substantially in vivo and requires only incubation of two cultures of bacterial cells, one containing the donor plasmid and one containing the host vector. In specific embodiments, this is a brief incubation, such as one or two hours, and then selection can be applied. This circumvents the need for DNA preparation of the donor clones that is required in all commercially available systems. The ability to carry out the recombination in vivo obviates the need to use expensive enzymes, so the method is cheaper. This method can in principle be used in a replica-plating strategy, which means that small labs can handle clone sets stored in 96-well or 384-well formats. This would allow many to have access to genomics at a considerably reduced expense. It should also be noted that plasmids can be transferred to eukaryotes from bacteria by mating, and it is conceivable that whole gene sets could be transferred to other species without ever preparing DNA and performing transfections. Plasmids have been successfully transferred to yeast by a replica-plating strategy, thus making genome-wide two hybrid screens via mating feasible.

A skilled artisan recognizes that the present invention, in a specific embodiment, is directed to a recombination system wherein regulatory elements are homologously recombined in vivo to the proximity of a polynucleotide of interest in an operably linked manner. In other specific embodiments, the homologous recombination of the polynucleotide of interest into the recipient vector maintains a reading frame, wherein additional elements are added either to the N terminus or the C terminus. Examples of these elements include a his tag, a GST tag, a myc tag, or an HA tag.

The invention also provides for additional embodiments. For example, PCR fragments comprising the approximately 50 bp homology have been directly subcloned in vivo by electroporation into a host plasmid-containing strain under optimal recombination conditions. This means that there may be complete elimination of any in vitro manipulations with enzymes in the entire process from cDNA entry to transfer. This ability to subclone in vivo could mean that this system could be converted from a mating system to a straight transformation system using donor clones or PCR derived fragments if desired.

A skilled artisan recognizes that the invention is flexible. The system has a number of features that distinguish it from existing systems. The first is that it is recombination sequence independent and can utilize any adaptor sequence so that the extra amino acids added to a protein can be chosen based on their desired properties, not by the sequences required by any site-specific recombinase. Secondly, the system is actually compatible with other systems in the art and could be combined with them to provide greater utility. For example, it would be simple to make the donor cloning vector compatible with the Univector/Echo system by including a loxP or loxH site upstream of the 5' homology adaptor sequence. A skilled artisan recognizes site-specific recombinase machinery would still not be required in this embodiment, given that recombination with these sites could occur by homologous recombination under suitable conditions.

In one embodiment, the present invention addresses a method of DNA transfer, comprising introducing a polynucleotide of interest having two homology regions into an E. coli bacteria, wherein the bacteria comprises a vector having a first homology region; a double strand break; and a second homology region; and homologously recombining the polynucleotide of interest into the vector at the homology regions.

In another embodiment the present invention there is a method of DNA transfer in vivo, comprising the steps of conjugating a first bacteria and a second bacteria, wherein a donor vector having a polynucleotide of interest in the first bacteria transfers to the second bacteria; and inserting the polynucleotide of interest from the donor vector into a recipient vector in the second bacteria, wherein the insertion occurs by homologous recombination. In another embodiment, the DNA is transferred through bacterial conjugation from a first vector in a first bacteria into a second vector in a second bacteria. The transfer preferably does not occur into the chromosome of the second bacteria, although in an alternative embodiment it may occur into a chromosome or a phage within the bacteria. A skilled artisan recognizes that transfer into the bacteria may occur by any feasible method in the art, including electroporation, phage infection (also referred to as phage transfer), mating, or calcium chloride transformation.

The present invention is not limited by the nature of the origin of replication employed on a vector. A variety of non-conditional origins of replication are known in the art and, in some embodiments, such as for the recipient vectors, they may be utilized. The invention is also not limited by the nature of any promoter element that may be employed. Those skilled in the art know that the choice of the promoter element depends upon the type of host cell to be utilized for expressing a gene(s) under the transcriptional control of the chosen promoter element. A wide variety of promoter elements functional in prokaryotic (e.g., E. coli) and eukaryotic (e.g., yeast, insect, mammals including humans) cells are known to the art and may be employed in the nucleic acid constructs of the present invention. Finally, a skilled artisan recognizes that the invention is not limited by the nature of any conditional promoter or conditional toxic gene that may be employed. Examples of such are well known in the art, and the choices thereof depend on a number of factors known to a skilled artisan.

In still other embodiments, the present invention does not require a toxic gene or a double strand break in the recipient vector. In some embodiments, the donor vector comprises a double strand break, the recipient vector requires a double strand break, or both the donor vector and recipient vector comprise a double strand break.

In one embodiment of the present invention, there is a bacteria cell generated through methods described herein. In a specific embodiment, the bacteria cell comprises a vector utilized in a method of the present invention.

In other embodiments, the present invention comprises a kit comprising a system described herein or for use in performing methods described herein. In some embodiments the vectors described herein are present in the bacteria of some kits, and in other embodiments the vectors of the kits are not comprised in bacteria. In some embodiments, a bacteria is not provided in the kit but is available through other means.

U.S. Pat. No. 6,376,192 is incorporated by reference herein in its entirety.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein. The following figures and discussion are directed to specific embodiments of the present invention. A skilled artisan is aware that these embodiments are merely exemplary and are not intended as limitations of the scope. Changes therein and other uses will occur to those skilled in the art which are encompassed within the spirit of the invention.

FIG. 6 shows liberation of an expression vector following exposure to arabinose, wherein the vector is flanked by the two distinct 50 bp regions of homology

DETAILED DESCRIPTION OF THE INVENTION

Figure 1:
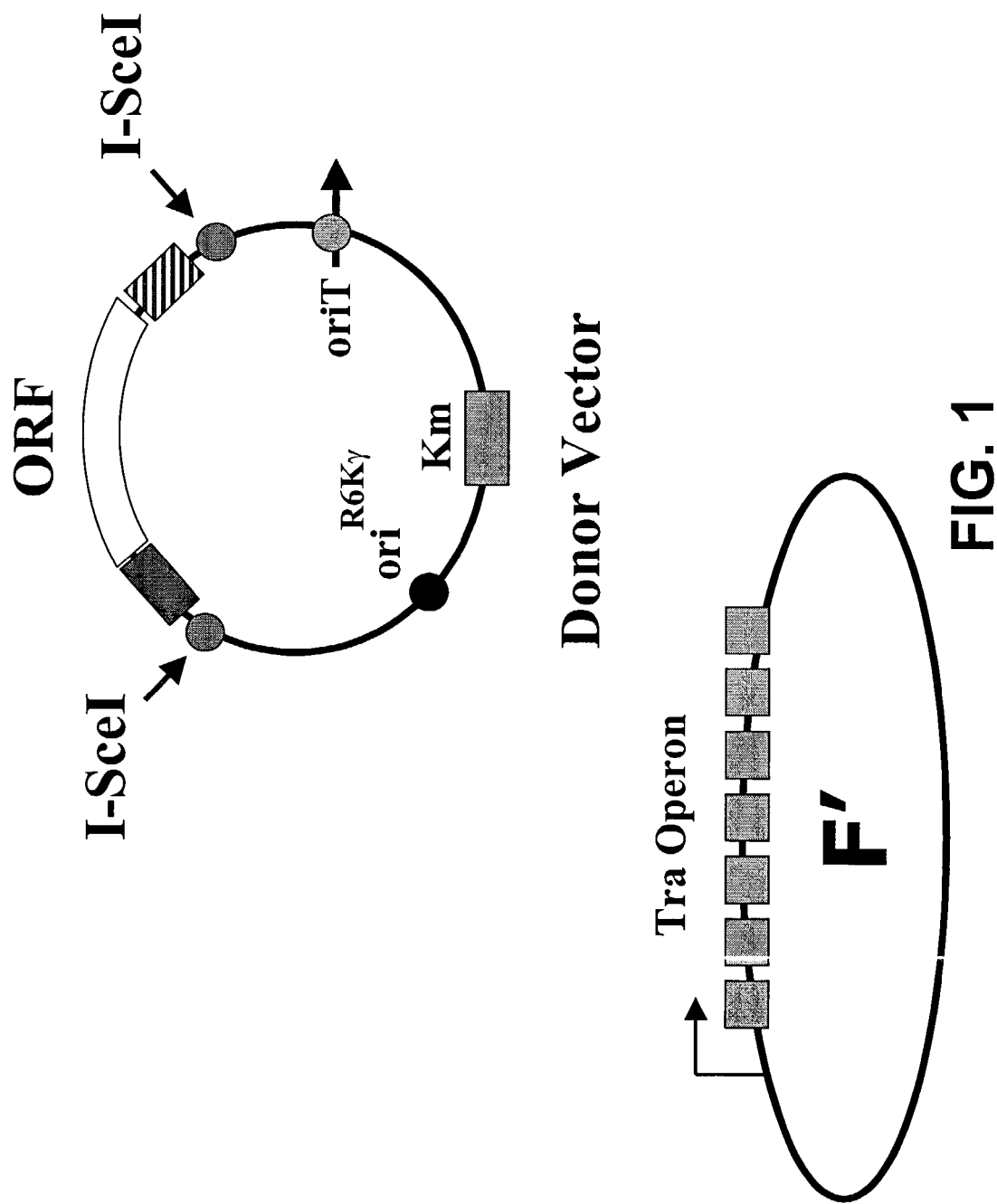
FIG. 1 illustrates a donor vector for ORF liberation in strain A.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

I. Definitions

In keeping with long-standing patent law convention, the words "a" and "an" when used in the present specification in concert with the word comprising, including the claims, denote "one or more."

As used herein, "a conditional origin of replication" refers to an origin of replication that requires the presence of a functional trans-acting factor (e.g., a replication factor) in a prokaryotic host cell. Conditional origins of replication encompass temperature-sensitive replicons such as rep pSC101$^{ts}$. Other examples include the RK2 oriV from RK2, the bacteriophage P1 ori, the origin of replication of the plasmid pSC101, the bacteriophage lambda ori, and so forth.

The term "cloning" as used herein is referred to as inserting a polynucleotide into another polynucleotide. Specifically, the term as used herein is directed to homologously recombining a polynucleotide of interest into another polynucleotide, such as a vector. The polynucleotide of interest may be a region from a vector, a polymerase chain reaction product, a restriction fragment, and so forth. In a specific embodiment, the cloning step lacks utilization of one or more restriction enzymes.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can comprise a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. Thus, nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In the present invention, the donor plasmid is preferably not an expression vector.

The term "homology region" as used herein is defined as a region in which homologous recombination can occur. The region may be about 30 to about 60 bp, and is preferably about 50 bp. A skilled artisan recognizes that the region does not need to be sequence-specific, such as having a lox or att site, and this is an advantage over the related art. A skilled artisan also recognizes that the corresponding homology regions selected between the donor and recipient vectors should be compatible, permitting homologous recombination to occur.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "meganuclease" as used herein refers to a restriction endonuclease having a very long recognition sequence. In a specific embodiment, the meganuclease recognition sequence comprises at least about 12 nucleotides. In a further specific embodiment, the recognition sequence comprises about 18 nucleotides.

As used herein, the term "origin of replication" refers to an origin of replication that is functional in a broad range of prokaryotic host cells (i.e., a normal or non-conditional origin of replication such as the ColEl origin and its derivatives).

As used herein, the term "promoter/enhancer" denotes a segment of DNA that comprises sequences capable of providing both promoter and enhancer functions (i.e., the functions provided by a promoter element and an enhancer element, see below for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Transcriptional control signals in eukaryotes comprise "promoter" and "enhancer" elements. Promoters and enhancers consist of short arrays of DNA sequences that interact specifically with cellular proteins involved in transcription (Maniatis et al., 1987). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al. (1986) and Maniatis et al. (1987)). For example, the SV40 early gene enhancer is very active in a wide variety of cell types from many mammalian species and has been widely used for the expression of proteins in mammalian cells (Dijkema et al., 1985). Two other examples of promoter/enhancer elements active in a broad range of mammalian cell types are those from the human elongation factor 10 gene (Uetsuki et al. (1989); Kim et al. (1990); Mizushima and Nagata, (1990)) and the long terminal repeats of the Rous sarcoma virus (Gorman et al. 1982) and the human cytomegalovirus (Boshart et al., 1985).

The term "rare restriction enzyme site" as used herein refers to a restriction site whose recognition site is about 8 bp or greater. In a specific embodiment, the rare restriction enzyme is a meganuclease. In another specific embodiment, the rare restriction enzyme is I-SceI.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

As used herein, the terms "selection marker," "selectable marker" or "selectable marker gene" refer to the use of a gene that encodes an enzymatic activity that confers the ability to grow in medium lacking what would otherwise be an essential nutrient (e.g., the TRP1 gene in yeast cells); in addition, a selectable marker may confer resistance to an antibiotic or drug upon the cell in which the selectable marker is expressed. A selectable marker may be used to confer a particular phenotype upon a host cell. When a host cell must express a selectable marker to grow in selective medium, the marker is said to be a positive selectable marker (e.g., antibiotic resistance genes that confer the ability to grow in the presence of the appropriate antibiotic). Selectable markers can also be used to select against host cells comprising a particular gene (e.g., the sacB gene which, if expressed, kills the bacterial host cells grown in medium containing 5% sucrose); selectable markers used in this manner are referred to as negative selectable markers or counter-selectable markers. Some examples of antibiotic resistance markers include resistance genes to kanamycin, ampicillin, tetracycline, chloramphenicol, spectinomycin, gentamycin, zeomycin, or streptomycin. Some examples of nutritional markers include trpA, trpB, proA, his3, ura3, or leu2.

The terms "sequence-specific recombinase target site" and "site-specific recombinase target site" refer to at least one short nucleic acid site or sequence that is recognized by a sequence- or site-specific recombinase and that becomes the crossover regions during the site-specific recombination event. Examples of sequence-specific recombinase target sites include, but are not limited to, lox sites, frt sites, att sites and dif sites. However, in preferred embodiments, site-specific recombinase target sites are not utilized with site-specific recombinase machinery but are used as homologous recombination sites.

The term "unique restriction enzyme site" indicates that the recognition sequence for a given restriction enzyme appears preferably only once within a nucleic acid molecule.

As used herein, the term "vector" is used in reference to nucleic acid molecules that transfer DNA segment(s) from one cell to another. The term "vehicle" is sometimes used interchangeably with "vector." A "vector" is a type of "nucleic acid construct." The term "nucleic acid construct" includes circular nucleic acid constructs such as plasmid constructs, plasmid constructs, cosmid vectors, etc. as well as linear nucleic acid constructs (e.g., λ phage constructs, PCR products). The nucleic acid construct may comprise expression signals such as a promoter and/or an enhancer (in such a case it is referred to as an expression vector). A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques (see, for example, Maniatis et al., 1988 and Ausubel et al., 1994, both incorporated herein by reference).

II. The Present Invention

The present invention is directed to a method of transferring a polynucleotide of interest, such as a DNA segment, from one vector to another.

In a general embodiment, there is a method of DNA transfer, comprising introducing a polynucleotide of interest having two homology regions into an *E. coli* bacteria, wherein the bacteria comprises a vector having a first homology region; a double strand break; and a second homology region; and homologously recombining the polynucleotide of interest into the vector at the homology regions, although in some embodiments the double strand break is not required. Thus, the polynucleotide of interest may be present on a plasmid, may be a polymerase chain reaction product, may be a restriction fragment, or may be present on a phagemid. The polynucleotide of interest may be transferred into a bacteria comprising the recipient vector by, for example, electroporation or by transformation. In one specific embodiment, the donor vector comprises a M13 origin.

In a preferred embodiment, a first vector is present in a first bacteria and comprises a polynucleotide of interest flanked by a unique (to the vector), rare restriction enzyme digestion site and homology regions. The first vector is transferred by bacterial conjugation to a second bacteria, followed by excision of the polynucleotide of interest from the first vector and then homologous recombination into the recipient second vector in the second bacteria. Various bacterial genetic embodiments are utilized in the present invention regarding such aspects as selective transfer of the first vector, selection against the first strain following transfer of the first vector, and selection for the second strain following homologous recombination of the polynucleotide of interest into the recipient second vector.

A skilled artisan recognizes that any background, environment, or reagent capable of providing homologous recombination is useful in the present invention. Lambda recombination gene products are utilized in some embodiments, whereas in others a suitable alternative means is provided, such as a recD strain, a recB sbcA strain, or a recB sbcB strain. Although the present invention requires that homologous recombination machinery be utilized, and that this is a significant advantage over other methods in the art, a skilled artisan recognizes that numerous recombination systems from various organisms have been described, including loxP, loP2, loxP3, loxP23, loxP511, loxB, loxC2, loxL, loxR, loxΔ86, loxΔ117, frt, dif, and att. See, e.g., Hoess et al., Nucleic Acids Research 14(6):2287 (1986); Abremski et al., J. Biol. Chem. 261(1):391 (1986); Campbell, J. Bacteriol. 174(23):7495 (1992); Qian et al., J. Biol. Chem. 267(11):7794 (1992); Araki et al., J. Mol. Biol. 225(1):25 (1992); Maeser and Kahnmann Mol. Gen. Genet. 230:170-176) (1991); Esposito et al., Nucl. Acids Res. 25(18):3605 (1997). In specific embodiments, the recombinase belongs to the integrase family of recombinases (Argos et al. EMBO J. 5:433-440 (1986)), examples of which include the Integrase/att system from bacteriophage lambda (Landy, A. Current Opinions in Genetics and Devel. 3:699-707 (1993)), the Cre/loxP system from bacteriophage P1 (Hoess and Abremski (1990) In Nucleic Acids and Molecular Biology, vol. 4. Eds.: Eckstein and Lilley, Berlin-Heidelberg: Springer-Verlag; pp. 90-109), and the FLP/FRT system from the *Saccharomyces cerevisiae* 2μ circle plasmid (Broach et al. Cell 29:227-234 (1982)). A skilled artisan recognizes the advantages of the present invention in utilizing homologous recombination instead of site-specific recombination. If a site-specific recombination site is utilized for recombination in the present invention, such as for compatibility with other systems in the art, homologous recombination with those sites is utilized and not site-specific recombination.

III. Conditional Origins of Replication and Suitable Host Cells

In specific embodiments of the present invention, the donor vector comprises a conditional origin of replication. Conditional origins of replication are origins that require the presence or expression of a trans-acting factor in the host cell for replication. A variety of conditional origins of replication functional in prokaryotic hosts (e.g., *E. coli*) are known to the art. The present invention is illustrated but not limited by the use of the R6Kγ origin, oriR, from the plasmid R6K. The R6Kγ origin requires a trans-acting factor, the II protein supplied by the pir gene Metcalf et al. (1996). *E. coli* strains containing the pir gene will support replication of R6Kγ origins to medium copy number. A strain containing a mutant allele of pir, pir-116, allows an even higher copy number of constructs containing the R6Kγ origin.

*E. coli* strains that express the pir or pir-116 gene product include BW18815 (American Type Culture Collection (referred to hereafter as ATCC) ATCC 47079; this strain contains the pir-116 gene), BW19094 (ATCC 47080; this strain contains the pri gene), BW20978 (this strain contains the pir-116 gene), BW20979 (this strain contains the pir gene), BW21037 (this strain contains the pir-116 gene) and BW21038 (this strain contains the pir gene) (Metcalf et al, supra).

Some other examples of conditional origins of replication suitable for use on the vectors of the present invention include:

1) the RK2 oriV from the plasmid RK2 (ATCC 37125). The RK2 oriV requires a trans-acting protein encoded by the trfA gene (Ayres et al., 1993);

2) the bacteriophage P1 ori which requires the repA protein for replication (Pal et al., 1986);

3) the origin of replication of the plasmid pSC101 (ATCC 37032) which requires a plasmid encoded protein, repA, for replication (Sugiura et al., 1992). The pSC101 ori also requires IHF, an *E. coli* protein. *E. coli* strains carrying the himA and himD (hip) mutants (the him and hip genes encode subunits of IHF) cannot support pSC101 replication (Stenzel et al., 1987);

4) the bacteriophage lambda ori which requires the lambda O and P proteins (Lambda II, Hendrix et al. Eds., Cold Spring Harbor Press, Cold Spring Harbor, N.Y. (1983);

5) pBR322 and other ColEI derivatives will not replicate in polA mutants of *E. coli* and therefore, these origins of replication need be used in a conditional manner (Grindley and Kelley (1976)); and 6) replication-thermosensitive plasmids such pSU739 or pSU300 which contain a thermosensitive replicon derived from plasmid pSC101, rep pSC101$^{ts}$ which comprises oriV (Mendiola and de la Cruz (1989); Francia and Lobo (1996)). pSU739 and pSU300 are stably maintained in *E. coli* strain DH5α (Gibco BRL) at a growth temperature of 30° C. (42° C. is non-permissive for replication of this replicon).

Other conditional origins of replication, including other temperature sensitive replicons, are known to the art and may be employed in the vectors and methods of the present invention.

Conditional origins, in some embodiments, would also comprise origins flanked by lox sites.

In one embodiment, a conditional origin of replication comprises an origin of replication flanked by recombination sites, such as site-specific recombination sites, and upon recombination the origin is deleted, leaving the molecule unable to replicate.

A skilled artisan recognizes that in some embodiments, the donor plasmid does not require a conditional origin of replication so long as there is a marker to select against the donor plasmid on its backbone that allows cells harboring it to be selected against.

IV. Promoters and Enhancers

In some embodiments, the polynucleotide of interest upon recombination into the recipient vector is operably linked to a suitable promoter for expression of the encoded gene product. Any promoter may be used, provided it allows expression in the respective expression system.

Those skilled in the art know that the choice of the promoter element depends upon the type of host cell to be employed for expressing a gene(s) under the transcriptional control of the chosen promoter element. A wide variety of promoter elements functional in prokaryotic (e.g., *E. coli*) and eukaryotic (e.g., yeast, insect, marimals including humans) cells are known to the art and may be employed in the nucleic acid constructs of the present invention.

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Suitable promoters include, but are not limited to, those obtained from cytomegalovirus (CMV), rous sarcoma virus (RSV), human immunodeficiency virus (HIV) long terminal repeat (LTR), and herpes simplex virus (HSV) thymidine kinase. Preferably, the promoter is the core SV40 early promoter. "R" and "U5" sequences which are located downstream of the transcription start site appear to be required for maximal expression from the HTLV-1 LTR (Fujisawa et al., 1986; Ohtani et al., 1987). The fusion of the R sequence and part of the U5 sequence (R-U5) from the HTLV-1 LTR to the SV40 promoter-enhancer has been found to increase the expression level of proteins more than an order of magnitude over that from the original SV40 promoter-enhancer (Takebe et al., 1988).

The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godhout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α$_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |

TABLE 1-continued

Promoter and/or Enhancer

| Promoter/Enhancer | References |
|---|---|
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al.,1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

V. Other Embodiments

Examples of workable combinations of cell lines and expression vectors are described in Sambrook et al. (1989); Ausubel et al. (1987); and Metzger et al. (1988). Many useful vectors are known in the art and many are commercially available from various vendors. Suitable promoters for use in prokaryotic hosts include, but are not limited to, the trp, lac and phage promoters, tRNA promoters and glycolytic enzyme promoters. Useful yeast promoters include, but are not limited to, the promoter regions for metallothionein, 3-phosphoglycerate kinase or other glycolytic enzymes such as enolase or glyceraldehyde-3-phosphate dehydrogenase and the enzymes responsible for maltose and galactose utilization. Appropriate mammalian promoters include, but are not limited to, the early and late promoters from SV40 (Fiers et al., 1978) and promoters derived from murine Moloney leukemia virus (MLV), mouse mammary tumor virus (MMTV), avian sarcoma viruses, adenovirus II, bovine papilloma virus and polyomas. In addition, the construct may be joined to an amplifiable gene so that multiple copies of the construct may be made. Amplifiable genes are known in the art and include, but are not limited to, the dihydrofolate reductase (DHFR) gene. For appropriate enhancer and other expression control sequences, see also Enhancers and Eukaryotic Gene Expression, Cold Spring Harbor Press: N.Y. (1983).

In some embodiments the donor vector may comprise a multiple cloning site (MCS). In other embodiments, the vector may comprise a start codon immediately 5' to the cloning site and a stop codon immediately 3' to the coding region. The vector may comprise signals including, but not limited to, a polyadenylation site 3' to the stop codon, and one or more enhancers. Any enhancer known in the art may be used. Suitable enhancers include, but are not limited to, the SV40 enhancer-promoter, the R-U5 segment of the HTLV-1 LTR, the CMV enhancer-promoter and any combination thereof. The CMV enhancer-promoter is described in Seed (1987). Preferably, the enhancer is the R-U5 segment of the HTLV-1 LTR and is 5' to the promoter.

In a preferred embodiment, a vector of the present invention is a shuttle vector, capable of replicating in at least two unrelated expression systems. In order to facilitate such replication, the vector must contain at least two origins of replication, one effective in each expression system. Typically, shuttle vectors are capable of replicating in a eukaryotic expression system and a prokaryotic expression system. This enables detection of protein expression in the eukaryotic host (the expression cell type) and amplification of the vector in the prokaryotic host (the amplification cell type). In some embodiments, one origin of replication is derived from SV40 and one is derived from pBR322, although any suitable origin known in the art may be used provided it directs replication of the vector.

Preferably, the vector comprises at least one nucleic acid sequence encoding a selectable marker. Preferably, where the vector is a shuttle vector, there are at least two selectable markers encoded, one for the expression cell type and one for the amplification cell type. Any selectable marker known in the art may be used provided it functions in the expression system being utilized. In one embodiment, a lac operator serves as a selectable marker. Suitable selectable markers for mammalian expression systems include, but are not limited to, G418 resistance and methotrexate resistance. Typical selection genes are known in the art and include, but are not limited to, those which encode proteins that: (a) confer resistance to antibiotics or other toxic substances including, but not limited to, ampicillin, neomycin, methotrexate; (b) complement auxotrophic deficiencies; or (c) supply critical nutrients not available from complex media, such as the D-alanine racemase for *Bacilli*. The choice of the proper selectable marker depends on the host cell, and appropriate markers for various hosts are well known. The present invention is not limited by the nature of the selectable marker gene chosen; the selectable marker may be a positive or negative selectable marker. In a preferred embodiment, the selectable marker is selected from the group consisting of the kanamycin resistance gene, the ampicillin resistance gene, the tetracycline resistance gene, the chloramphenicol resistance gene, the streptomycin resistance gene, the strA gene and the sacB gene.

The cloning site is preferably a multicloning site to allow for cloning gene fragments in all three reading frames. Any multicloning site can be used, including many that are commercially available. To facilitate expression of the gene fragment cloned into the multicloning site, the site may also include an excisable stop codon to limit background expression.

The DNA vectors of the present invention can be introduced into host cells by various methods known in the art. Such methods differ depending on the type of cellular host, and include, but are not limited to, electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al. (1989); and Ausubel et al. (1987). Reference herein to cells into which these DNA vectors have been introduced is intended also to include the progeny of such cells.

In some embodiments of the present invention, the donor vector has the R6K gamma DNA replication origin (oriR (R6K gamma) so they replicate only in bacteria supplying the pi replication protein (encoded by pir), and a skilled artisan recognizes they can be maintained at low or high plasmid copy number by using *Escherichia coli* strains encoding either wild-type or mutant forms of pi. In some embodiments, the vectors also carry the RP4 transfer origin (oriT(RP4)) so they can be transferred by conjugation to a broad range of bacteria. In specific embodiments they encode lacZ alpha for blue-white color screening of colonies for ones with plasmids carrying inserts, as well as the f1 DNA replication origin for preparation of single-stranded DNA. A skilled artisan also recognizes that a number of additional features (including the presence of multiple cloning sites flanked by T3 and T7 RNA polymerase promoters) make these plasmids useful as general cloning vectors as well.

A skilled artisan recognizes that, in general, the embodiments of the present invention utilizing bacterial conjugation comprise a donor plasmid in a bacteria having an F' (or wherein the F' is integrated into the bacteria, making it an Hfr bacteria) and a recipient vector, preferably an expression vector, having an inducibly expressed rare restriction enzyme. A skilled artisan also recognizes that, in an alternative embodiment, an origin of transfer may be present on the "expression vector" and this vector transfers into a bacteria comprising the donor plasmid and an inducibly expressed rare restriction enzyme. In some embodiments the lacZ alpha is present on the donor plasmid to identify successful completion of cloning into the vector, such as with a cDNA. In other embodiments, the lacZ alpha is utilized on the recipient vector to identify loss of a fragment upon homologous recombination.

In a specific embodiment, a vector of the present invention comprises a prokaryotic termination sequence. The present invention is not limited by the nature of the prokaryotic termination sequence chosen. In a further specific embodiment, the prokaryotic termination sequence is the T7 termination sequence.

A. Initiation Signals and Internal Ribosome Binding Sites

A specific initiation signal also may be required for efficient translation of coding sequences, and the vectors of the present invention may comprise one, in some embodiments. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

B. Multiple Cloning Sites

Vectors can include a MCS, which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

C. Splicing Sites

Some vectors of the present invention are suitable for use in a eukaryotic cell. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

D. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

E. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

F. Selectable and Screenable Markers

In certain embodiments of the invention, cells comprising a nucleic acid construct of the present invention may be identified in vitro or in vivo by including a marker in the expression vector, or their growth may be selected for or against by utilizing the marker. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Examples of selection markers being drug resistance markers include ampicillin, kanamycin, tetracycline, chloramphenicol, and streptomycin.

G. Plasmid Vectors

In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage may also contain, or be modified to contain, for example, promoters which can be used by the microbial organism for expression of its own proteins. A skilled artisan recognizes that any plasmid in the art may be modified for use in the methods of the present invention.

Bacterial host cells, for example, *E. coli*, comprising the vectors of the present invention, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. In some embodiments, after culturing the bacteria for a further period, generally of between 2 h and 24 h, the cells are collected by centrifugation and washed to remove residual media.

VI. Restriction Enzymes

Although an advantage of the present invention is the lack of requirement to perform restriction enzyme digestion specifically for transferring a polynucleotide from one vector to another, restriction enzyme digestion sites will be present in the vectors utilized herein. For example, in some embodiments a polynucleotide of interest is ligated into a donor vector prior to being subjected to the methods of the present invention.

Examples of restriction enzymes are provided in the following table:

| Name | Recognition Sequence |
|---|---|
| AatII | GACGTC |
| Acc65 I | GGTACC |
| Acc I | GTMKAC |
| Aci I | CCGC |
| Acl I | AACGTT |
| Afe I | AGCGCT |
| Afl II | CTTAAG |
| Afl III | ACRYGT |
| Age I | ACCGGT |
| Ahd I | GACNNNNNGTC (SEQ ID NO:1) |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN (SEQ ID NO:2) |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC (SEQ ID NO:3) |
| BciV I | GTATCC |
| Bcl I | TGATCA |
| Bfa I | CTAG |
| Bgl I | GCCNNNNNGGC (SEQ ID NO:4) |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC (SEQ ID NO:5) |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG (SEQ ID NO:6) |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC (SEQ ID NO:7) |
| BstB I | TTCGAA |
| BstE II | GGTNACC |
| BstF5 I | GGATGNN |
| BstN I | CCWGG |
| BstU I | CGCG |
| BstX I | CCANNNNNNTGG (SEQ ID NO:8) |
| BstY I | RGATCY |
| BstZ17 I | GTATAC |

-continued

| Name | Recognition Sequence |
|---|---|
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC (SEQ ID NO:9) |
| Eae I | YGGCCR |
| Eag I | CGGCCG |
| Ear I | CTCTTC |
| Eci I | GGCGGA |
| EcoN I | CCTNNNNNAGG (SEQ ID NO:10) |
| EcoO109 I | RGGNCCY |
| EcoR I | GAATTC |
| EcoR V | GATATC |
| Fau I | CCCGCNNNN (SEQ ID NO:11) |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| I-SceI | 5'TAGGGATAA^CAGGGTAAT3' (SEQ ID NO:12)<br>3'ATCCC^TATTGTCCCATTA5' (SEQ ID NO:13) |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN (SEQ ID NO:14) |
| Mnl I | CCTC |
| Msc I | TGGCCA |
| Mse I | TTAA |
| Msl I | CAYNNNNRTG (SEQ ID NO:15) |
| MspA1 I | CMGCKG |
| Msp I | CCGG |
| Mwo I | GCNNNNNNNGC (SEQ ID NO:16) |
| Nae I | GCCGGC |
| Nar I | GGCGCC |
| Nci I | CCSGG |
| Nco I | CCATGG |
| Nde I | CATATG |
| NgoMI V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG (SEQ ID NO:17) |
| PleI | GAGTC |
| Pme I | GTTTAAAC |
| Pml I | CACGTG |
| PpuM I | RGGWCCY |
| PshA I | GACNNNNGTC (SEQ ID NO:18) |
| Psi I | TTATAA |
| PspG I | CCWGG |
| PspOM I | GGGCCC |

-continued

| Name | Recognition Sequence |
|------|---------------------|
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC (SEQ ID NO:19) |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG (SEQ ID NO:20) |
| Xho I | CTCGAG |
| Xma I | CCCGGG |
| Xmn I | GAANNNNTTC (SEQ ID NO:21) |

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described, for example, in Sambrook et al. (1989).

EXAMPLES

The following examples are offered by way of example, and are not intended to limit the scope of the invention in any manner. A skilled artisan recognizes the following discussion is exemplary in providing reagents and methods of the present invention, and is aware that other embodiments may also be utilized.

Example 1

Donor Vector for ORF Liberation in Strain A

FIG. 1 illustrates a starting strain A for the embodiment that utilizes bacterial conjugation. In this strain, there preferably is a conjugation system for the transfer of the vector, and multiple conjugation systems are known in the art. In a specific embodiment, there is an F' and the donor plasmid comprises an origin of transfer that is recognized by the transfer proteins of the F'. In a specific embodiment, the F' has its origin of transfer deleted so that it can not mate into other strains. The strain also comprises a lambda lysogen carrying the pir-116 gene that supports the replication of the R6K origin on the donor plasmid. The donor plasmid comprises the ORF or the polynucleotide or gene of interest flanked by two different approximately 50 bp sequences that serve as the homology for the subsequent homologous recombination events used to transfer the ORF into a recipient plasmid. The genotype of the strain A is preferably F' pir116. In some embodiments, the genotype is F' (lac$^+$pro$^+$ ΔoriT::Tc). In other embodiments, the genotype of strain A is F' (lac$^+$pro$^+$ΔoriT::Tc) Δlac-169 rpoS(Am) robA1 creC510 hsdR514 ΔuidA(MluI)::pir-116 endA(BT333). The genotype of strain B is preferably umuC::P$^{BAD}$-I-SceI. In some embodiments, the genotype of strain B is lacI$^Q$ rrnB3 ΔlacZ4787 hsdR514 ΔaraBAD567 ΔrhaBAD568 galU95 ΔendA9::FRT ΔrecA635::FRT umuC::P$^{BAD}$-I-SceI-Kan. In one specific embodiment, the second bacteria is recA. In a specific embodiment, the second bacteria is recA and has polynucleotides encoding exo, β and gam recombination functions of bacteriophage λ. In other embodiments, the strain is a recD strain, a recB sbcA strain, or a recB sbcB strain.

Example 2

ORF Transfer by Conjugation Followed by Excision

Figure 2:
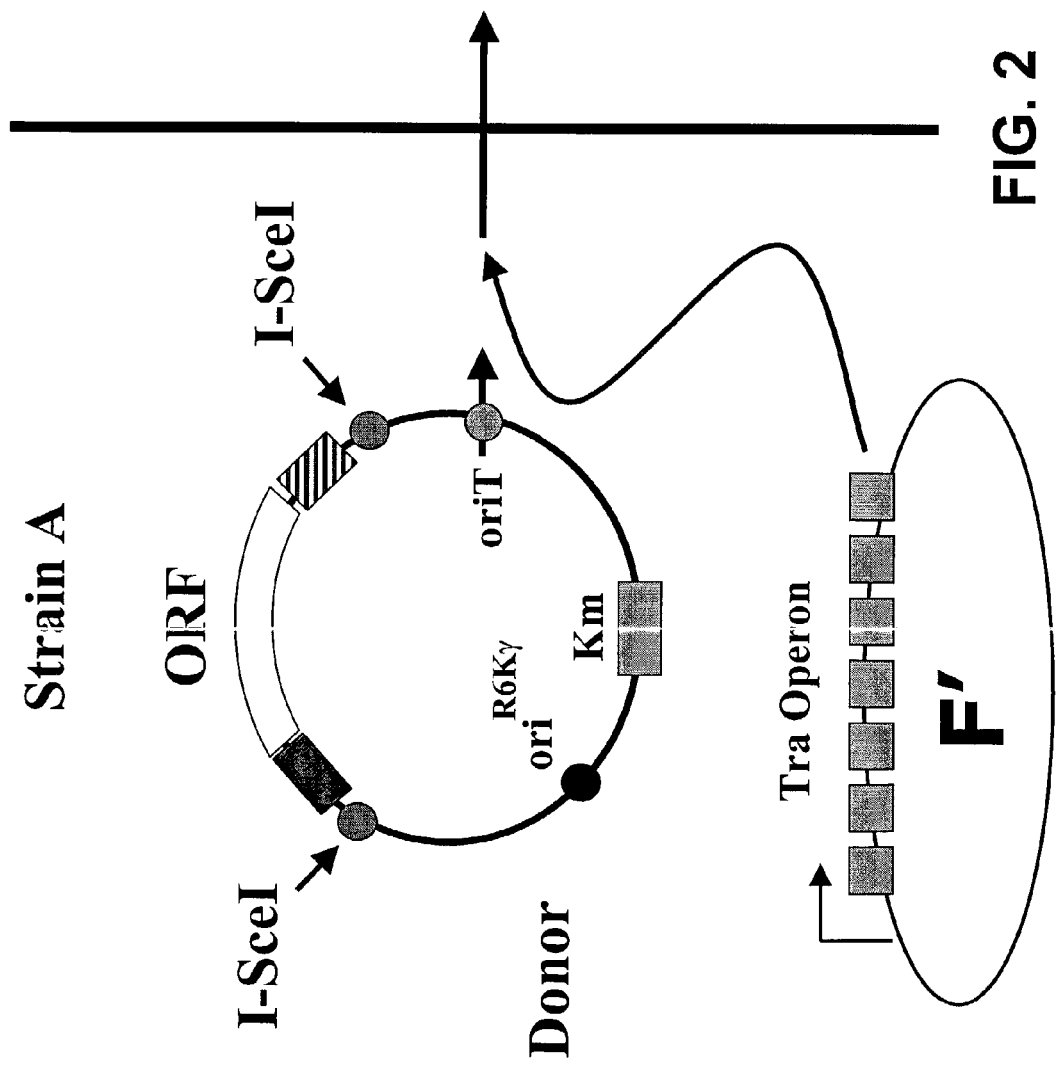
FIG. 2 shows the overall embodiment of ORF transfer by conjugation followed by excision, wherein the strain A is mixed with strain B, which lacks an F'.

FIG. 2 illustrates ORF transfer by conjugation, followed by excision. Upon mixing strain A with strain B, which lacks an F', the donor plasmid is transferred to strain B by conjugal transfer. Control experiments indicate that upon mixing strains A and B and allowing growth at about 30° C. for about two hours, 10% to 50% of strain B can acquire a donor plasmid. However, in this embodiment, strain B does not support the replication of the donor plasmid, because it lacks the pir1 gene required for the function of the R6Kγ origin to replicate.

Example 3

ORF Transfer by Conjugation Followed by Excision

Figure 3:
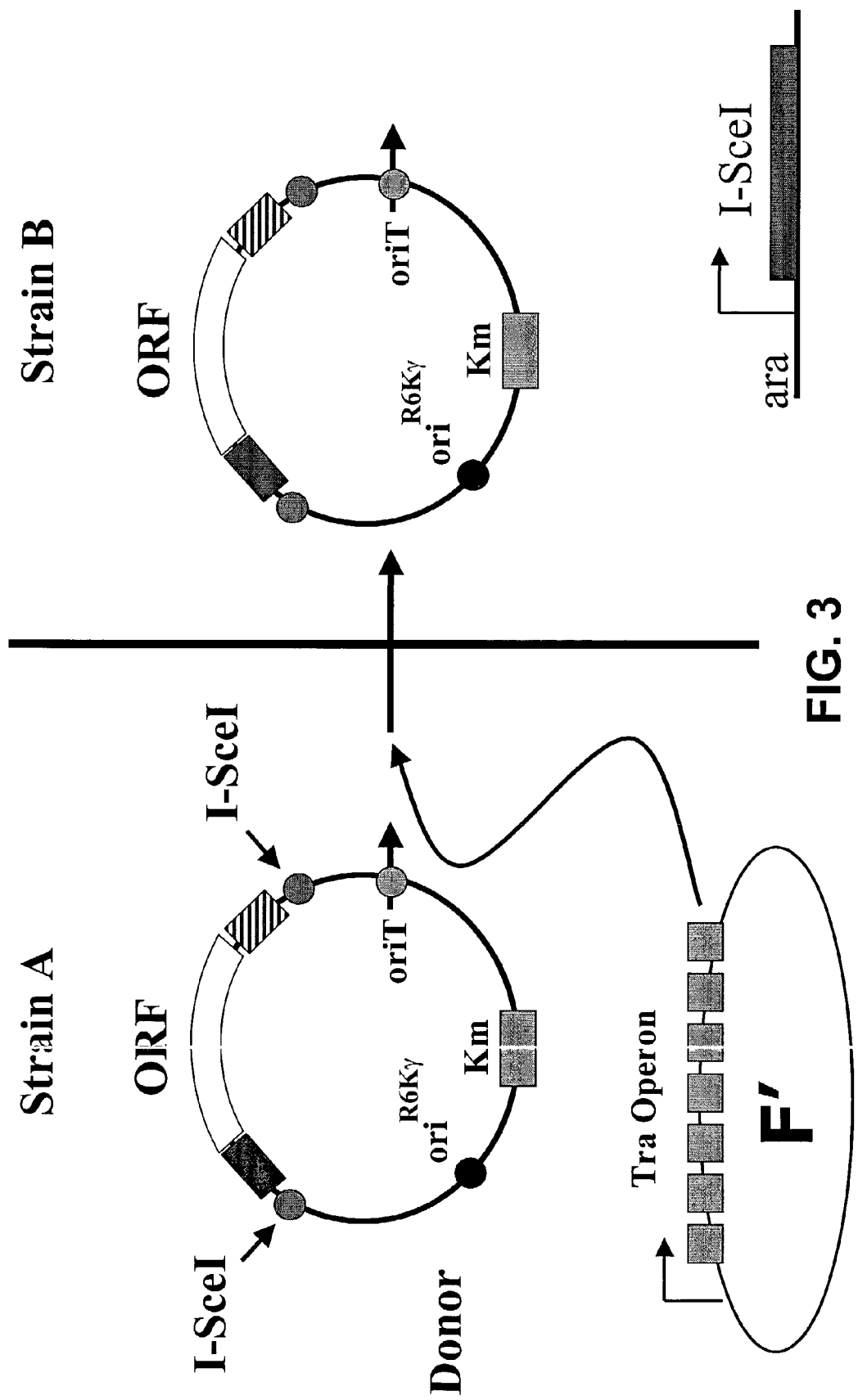
FIG. 3 illustrates the first step of ORF transfer by conjugation followed by excision, wherein the donor plasmid is transferred into strain B.

FIG. 3 illustrates the first step of ORF transfer by conjugation followed by excision, wherein the donor plasmid is transferred into strain B. A skilled artisan recognizes there are well-known methods in the art for bacterial mating, including those comprising liquid media or replica plating. Strain B also comprises the I-SceI restriction enzyme under the control of the araB promoter that is inducible when arabinose is added to the media.

Figure 4:
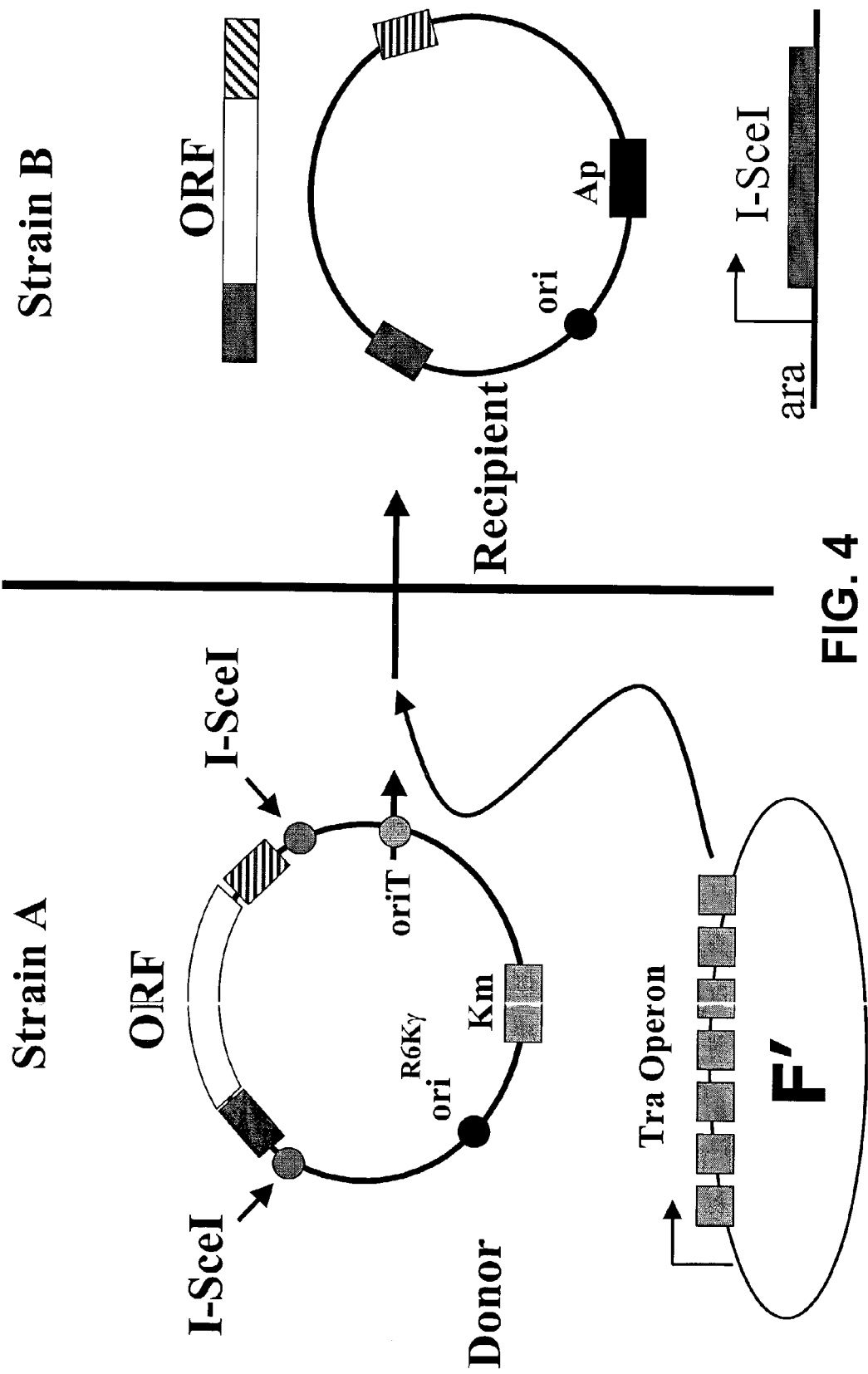
FIG. 4 shows the second step of ORF transfer by conjugation followed by excision. When arabinose is present, the I-SceI enzyme cuts the donor plasmid in two places, liberating the ORF flanked by two distinct 50 bp regions of homology to the recipient vector.

FIG. 4 shows the second step of ORF transfer by conjugation followed by excision. When arabinose is present, the I-SceI enzyme cuts the donor plasmid in two places, liberating the ORF flanked by two distinct 50 bp regions of homology to the recipient vector.

Example 4

Recipient Vector in Strain B

Figure 5:
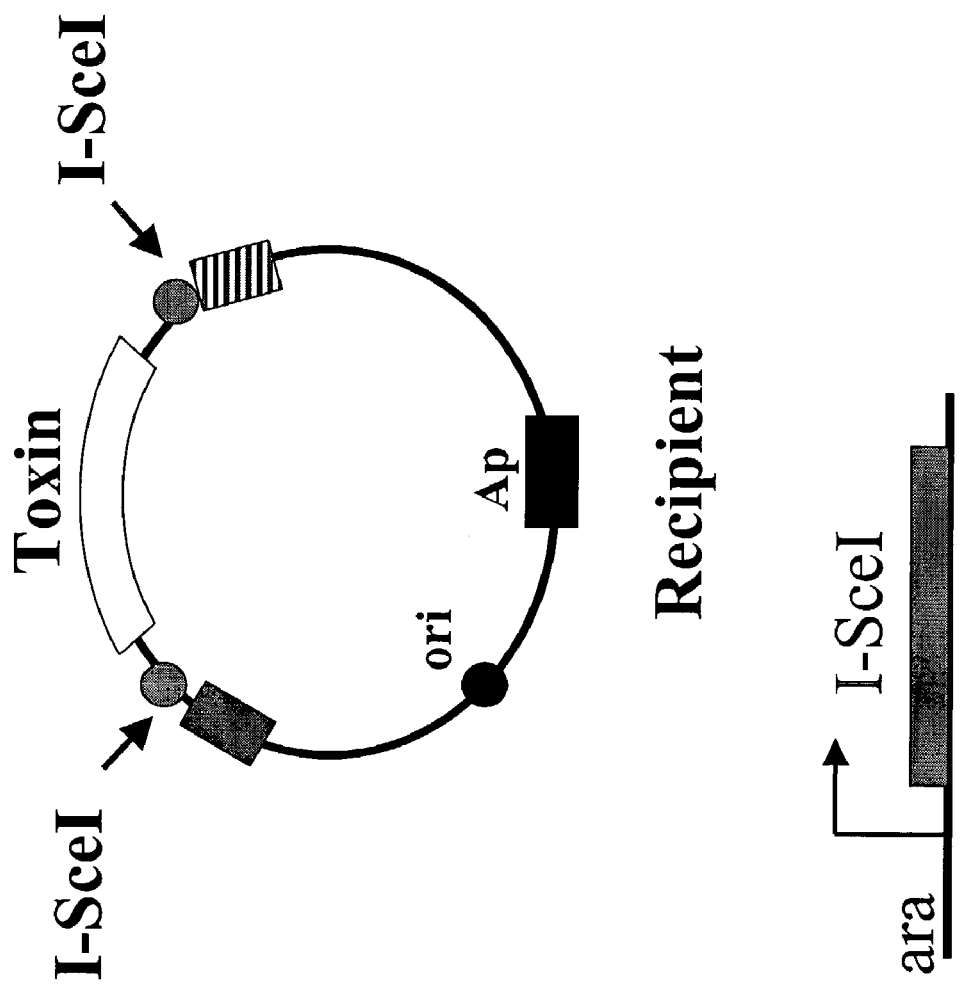
FIG. 5. illustrates a recipient vector in strain B.

FIG. 5. illustrates a recipient vector in strain B. The recipient plasmid is a typical expression vector into which the two homology regions of about 50 bp are inserted followed by I-SceI restriction sites that flank a toxin gene. The toxin gene in specific embodiments is the pheS mutation that broadens the specificity of the phenylalanine tRNA synthetase so that it can recognize C1-Phe, a potentially toxic amino acid analog if it can be charged onto tRNA$^{Phe}$ (Schneider et al., 1997). A skilled artisan recognizes that other conditional lethal toxic genes can be used alternatively. Examples include sacB, pyrF, and the tetracycline resistance gene. Strain B also comprises a Sp$^R$ plasmid pML104 that has the lambda recombination genes under lac promoter control on a pSC101Ts origin based plasmid. This plasmid can be eliminated from the strain by growth at about 42° C.

Figure 6:
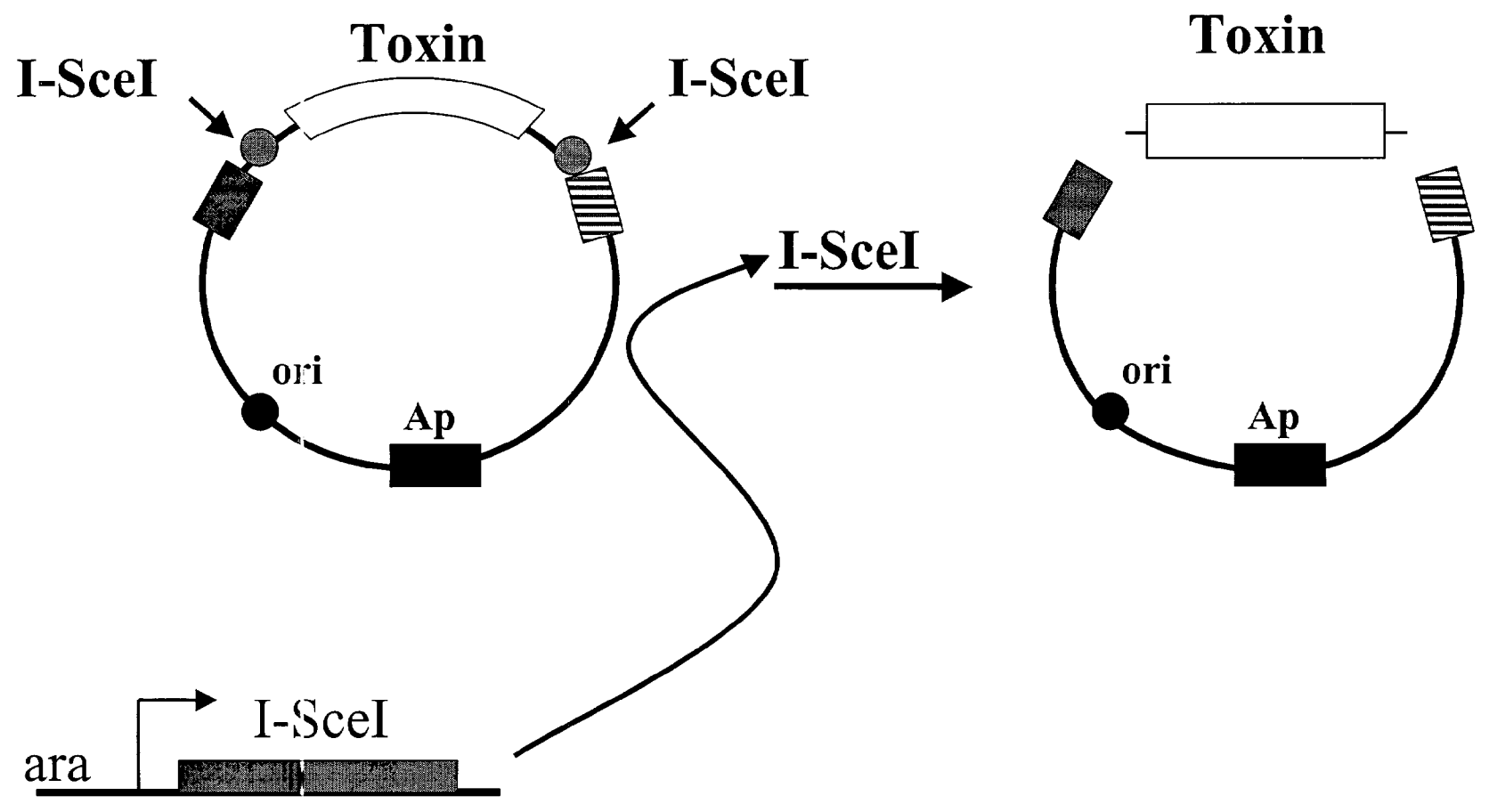
Figure 7:
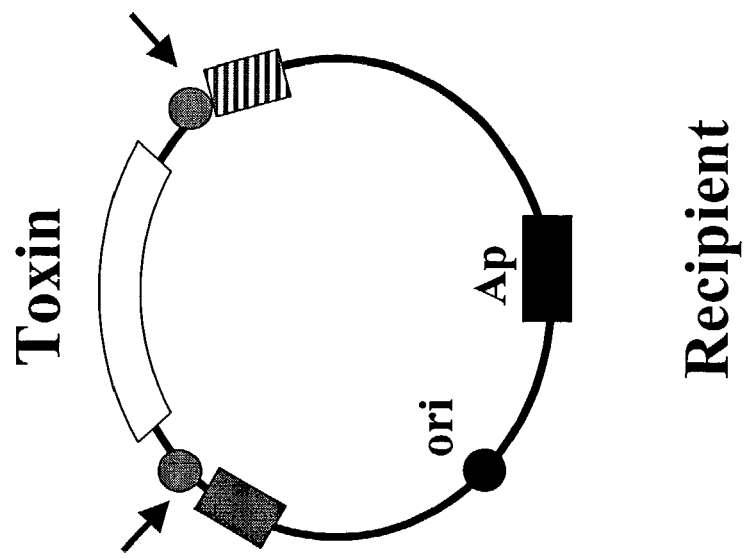
FIG. 7 shows strain B after conjugation.
Figure 7:
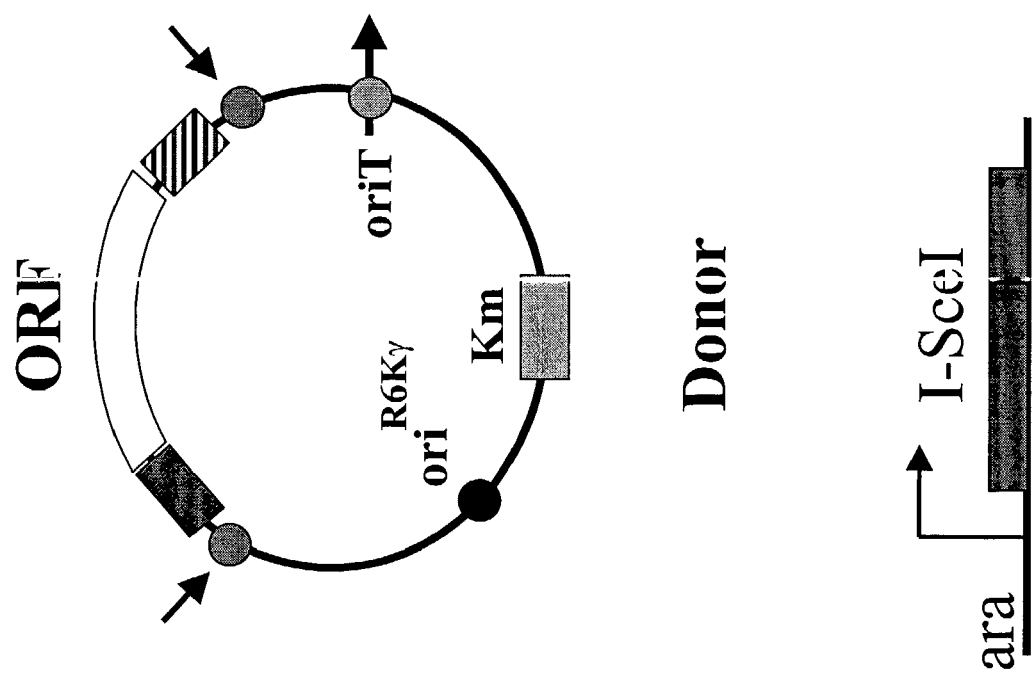

FIG. 6 shows liberation of an expression vector following exposure to arabinose, wherein the vector is flanked by the two distinct 50 bp regions of homology. FIG. 7 shows the new strain created after mating of the donor plasmid of strain A into strain B prior to induction of I-SceI.

Example 5

Figure 8:
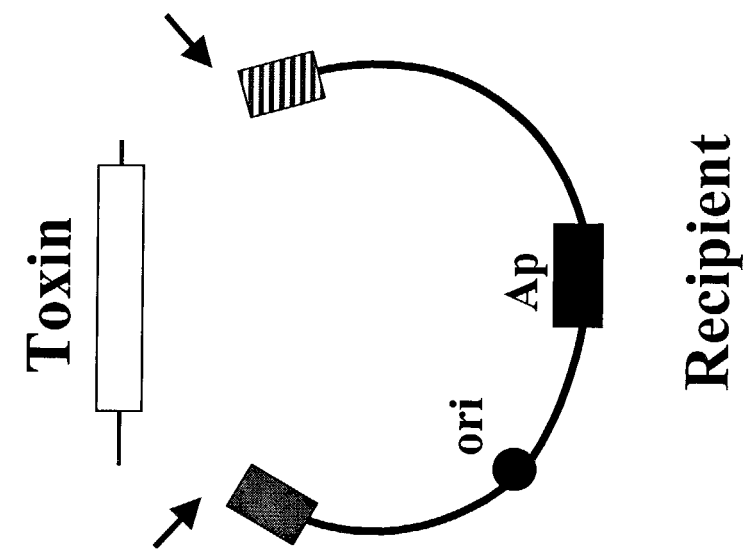
FIG. 8 shows strain B after conjugation and I-SceI induction.
Figure 8:
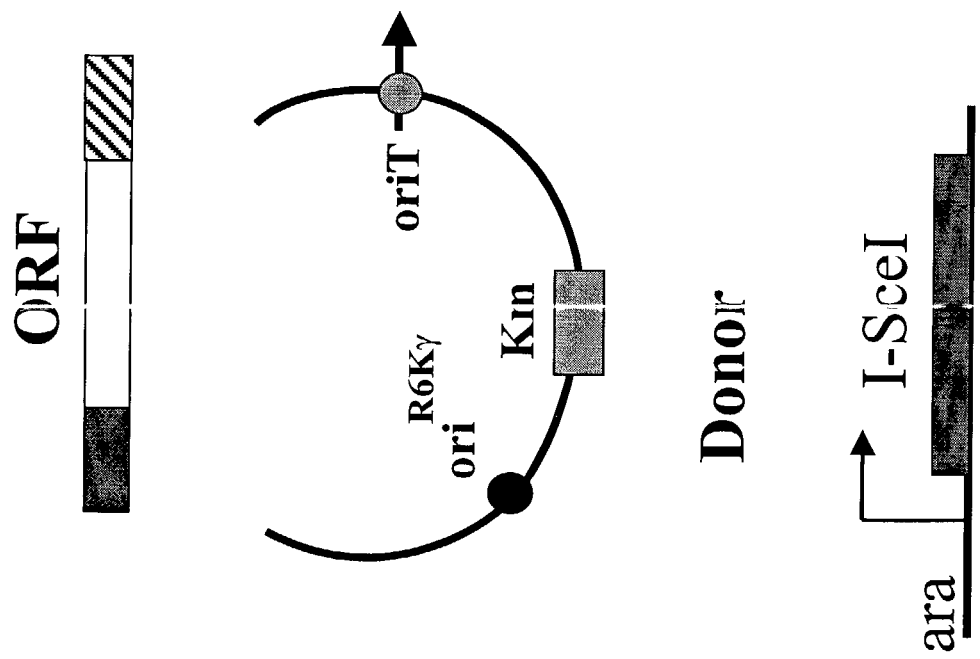
Figure 9:
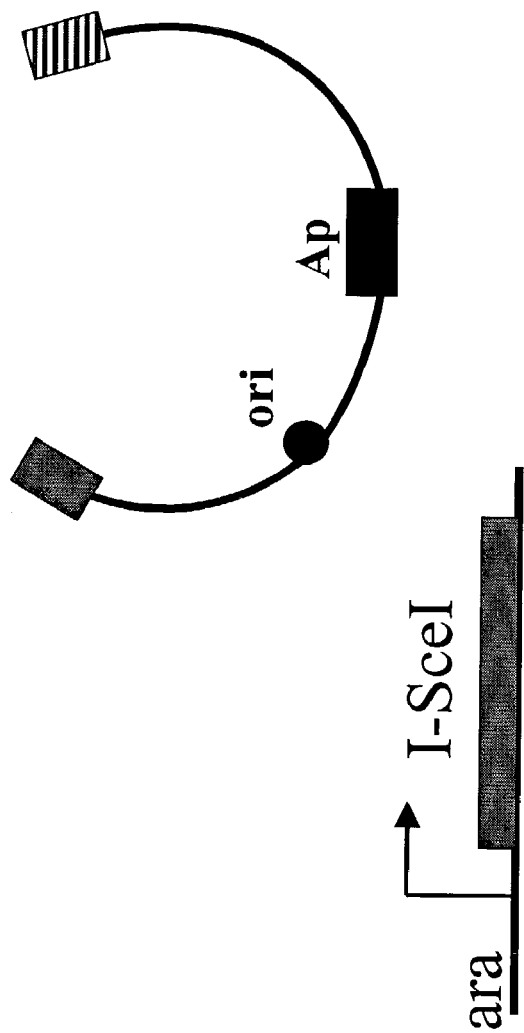
FIG. 9 illustrates the relevant recombination substrates produced by cleavage of the donor and recipient plasmids.
Figure 9:

Strain B after Conjugation and I-SceI Induction and Recombinant Vector Construction by Homologous Recombination In Vivo FIG. 8 represents the cleavage of the donor and recipient plasmids after I-SceI induction. FIG. 9 illustrates the relevant recombination substrates produced by cleavage of the donor and recipient plasmids.

Figure 10:
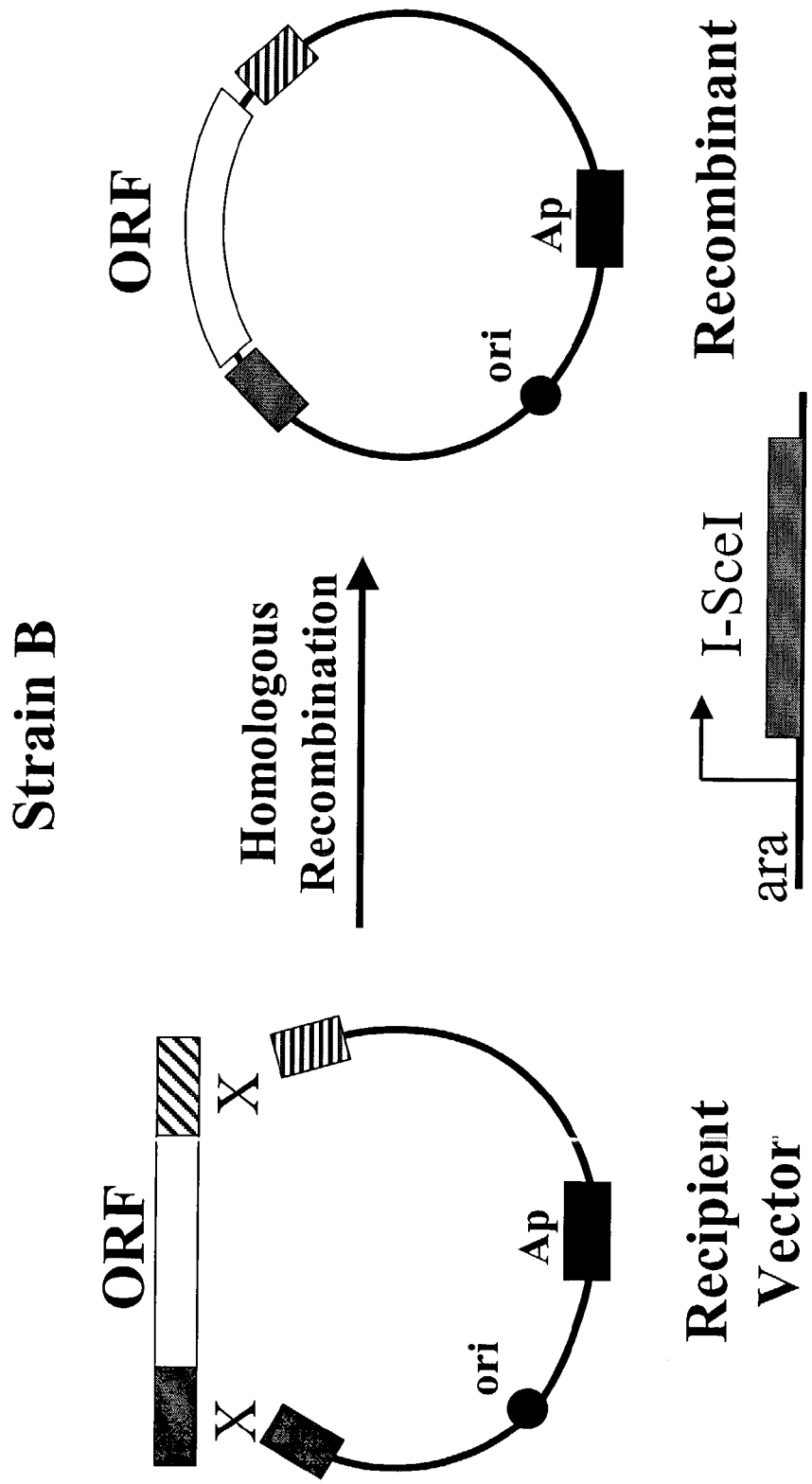
FIG. 10 shows recombinant vector construction by homologous recombination in vivo.

FIG. 10 shows recombinant vector construction by homologous recombination in vivo. Homologous recombination between the relevant fragments is catalyzed by recombination enzymes expressed from a Sp$^R$ plasmid in strain B. Recombination results in the recircularization of the recipient vector that now lacks I-SceI restriction sites so that it can now replicate in the presence of I-SceI enzymes. The recombination event is selected by growth on arabinose in the presence of Ap Km and C1-Phe. Ap selects for recircularization, and arabinose induces I-SceI, which cuts and destroys non-recombinant recipient plasmids. C1-Phe kills any cells that might have a mutant I-SceI gene or lost the I-sceI sites and therefore can maintain recipient plasmids containing the insert. Kanamycin helps select against strain A.

Example 6

Cloning DNA Products by Recombination

Figure 11:
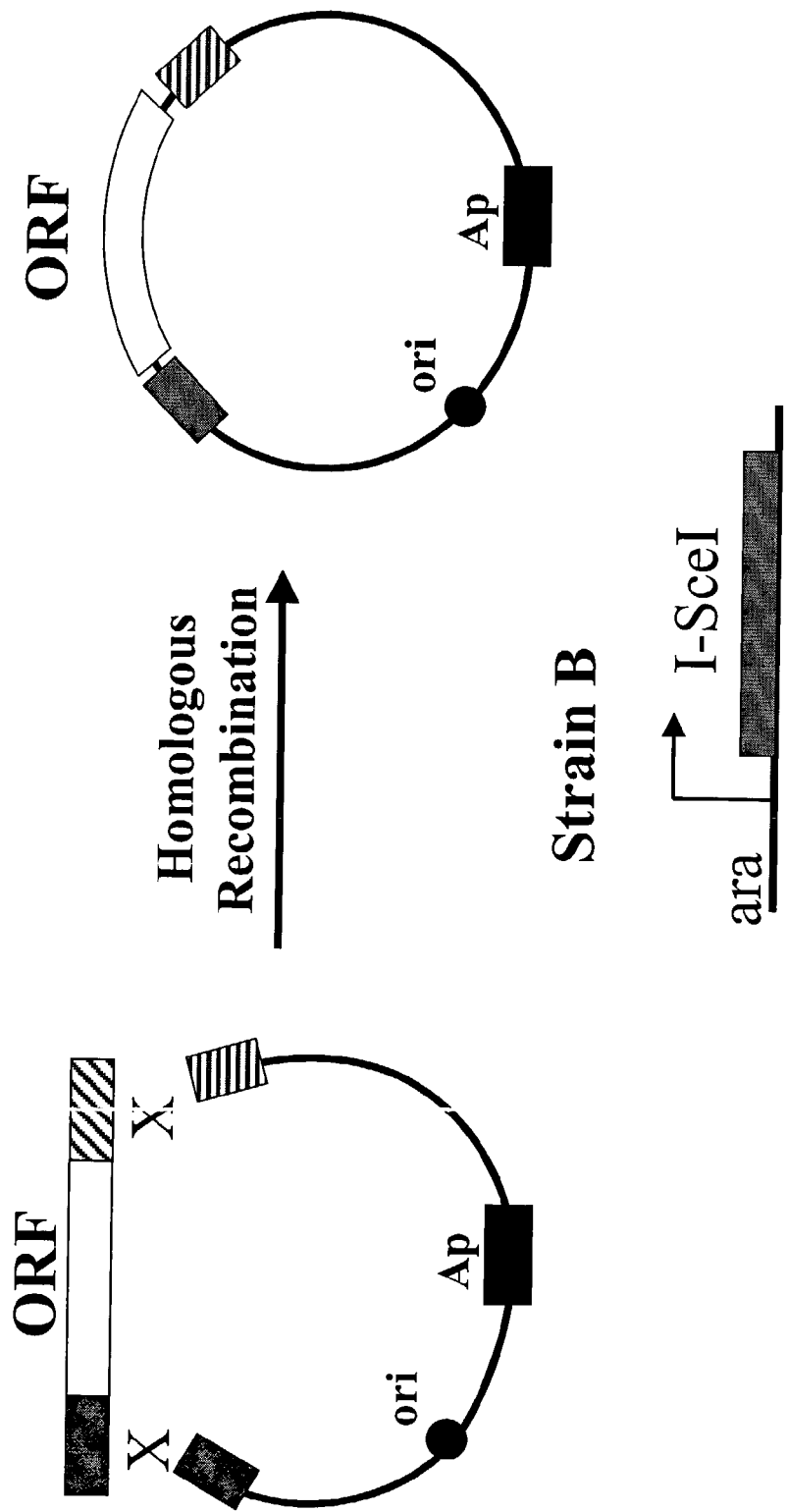
FIG. 11 illustrates cloning PCR fragments by recombination with the present invention.

In a specific embodiment, a DNA product of interest, such as a restriction enzyme fragment or a polymerase chain reaction product, is cloned directly into a strain B having an inducibly-regulated rare restriction enzyme and a recipient vector. FIG. 11 illustrates cloning PCR fragments by recombination with the present invention. In this embodiment, a PCR fragment is generated wherein at least a portion, such as the ends, comprises recombination sites. The PCR fragments are subcloned by introducing them directly into a bacteria comprising a recipient vector, having the respective homology regions, by means such as electroporation or CaCl$_2$ transformation. The recipient vector need not be linearized, in some embodiments. Homologous recombination then occurs between the polymerase chain reaction product and the recipient vector at the homology regions. Similar selection techniques as other embodiments described herein may be utilized. Experiments indicated that the subcloning by this method is 95% efficient.

Example 7

Another Embodiment having a Drug Resistance Gene Linked to the ORF

Figure 12:
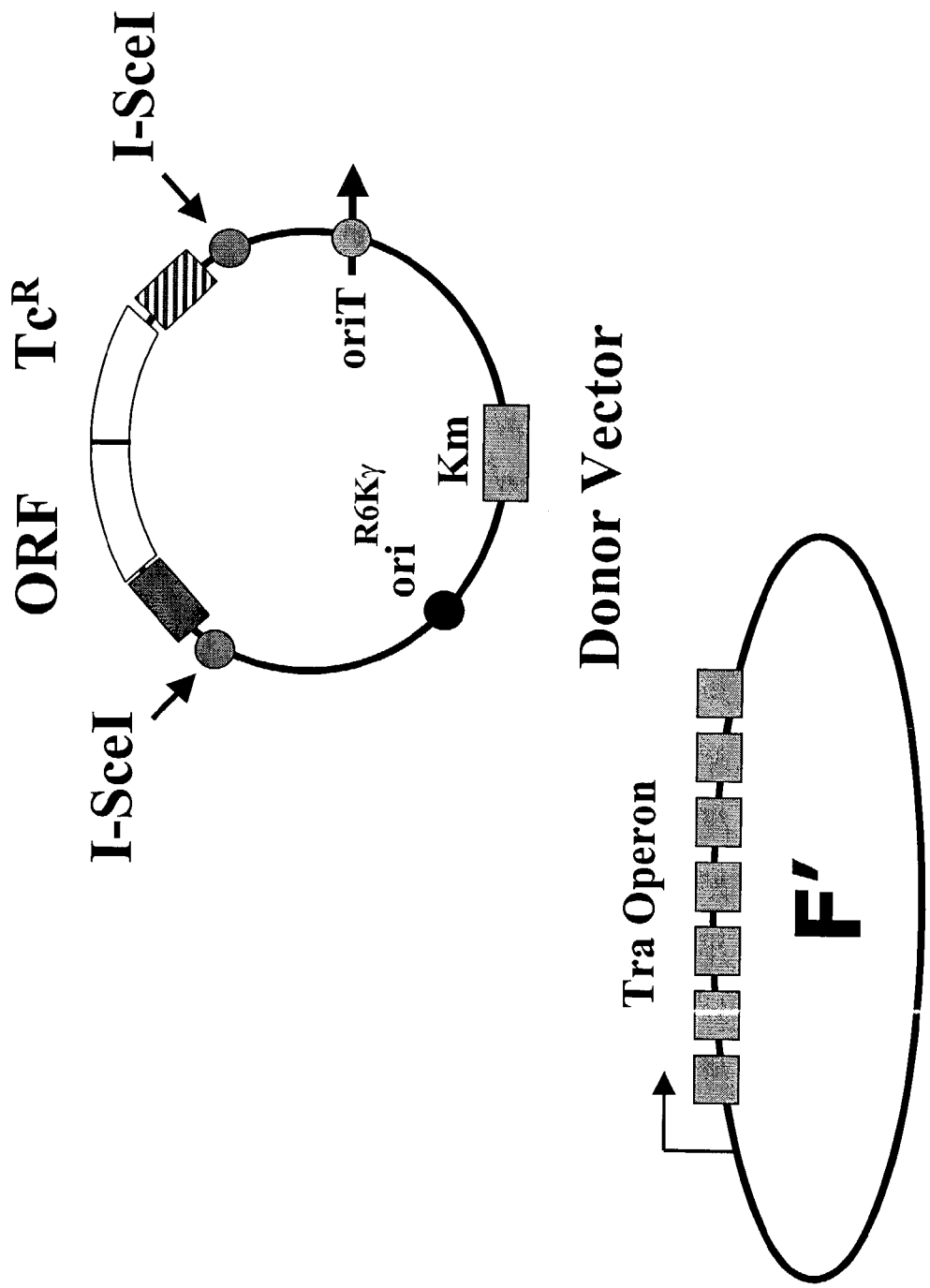
FIG. 12 shows an additional embodiment of the present invention having a drug resistance gene linked to the ORF.

FIG. 12 shows an additional embodiment of the present invention having a drug resistance gene linked to the ORF. In a specific embodiment, the ORF or gene of interest is linked to a drug marker such as tetracycline (Tc) that encodes tetracycline resistance. The transfer of this drug resistance into strain B forms the basis of the selection for transfer. In a specific embodiment, the system is useful for making N-terminal fusions. A skilled artisan recognizes that C-terminal fusions would require an additional step, such as site-specific recombination, to eliminate the drug marker and allow fusion proteins to be generated. The advantage to this embodiment is that it is 100% efficient and requires slightly less complex selection procedures.

Example 8

Enhancing Efficiency of the System

Figure 13:
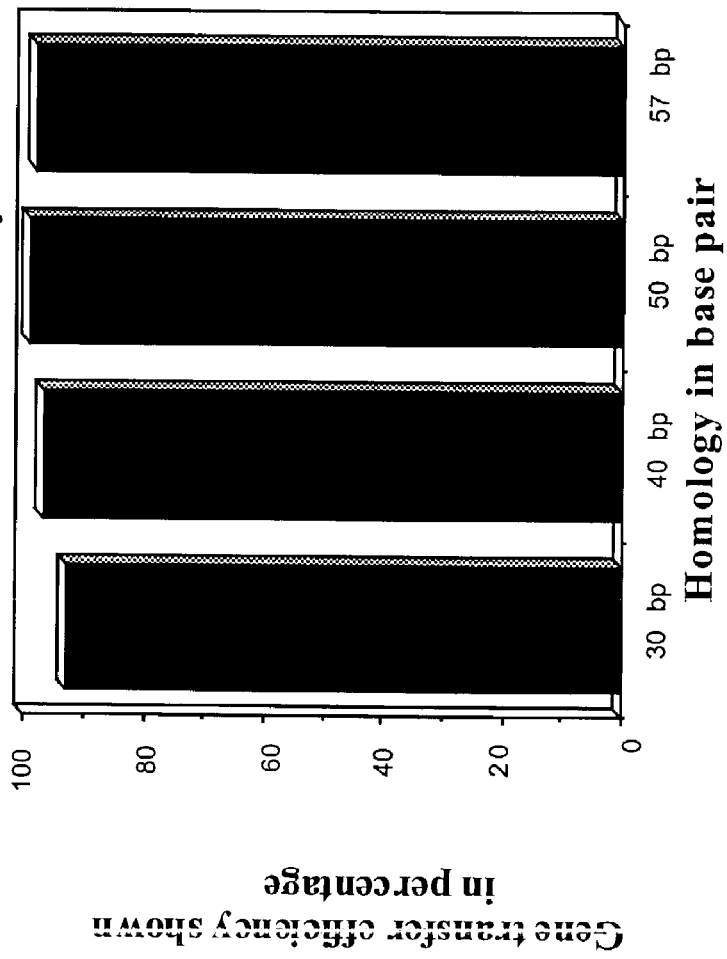
FIG. 13 shows the effect of the length of the homology region on gene transfer efficiency was studied, wherein counter-selection against pheS was utilized.
Figure 14:
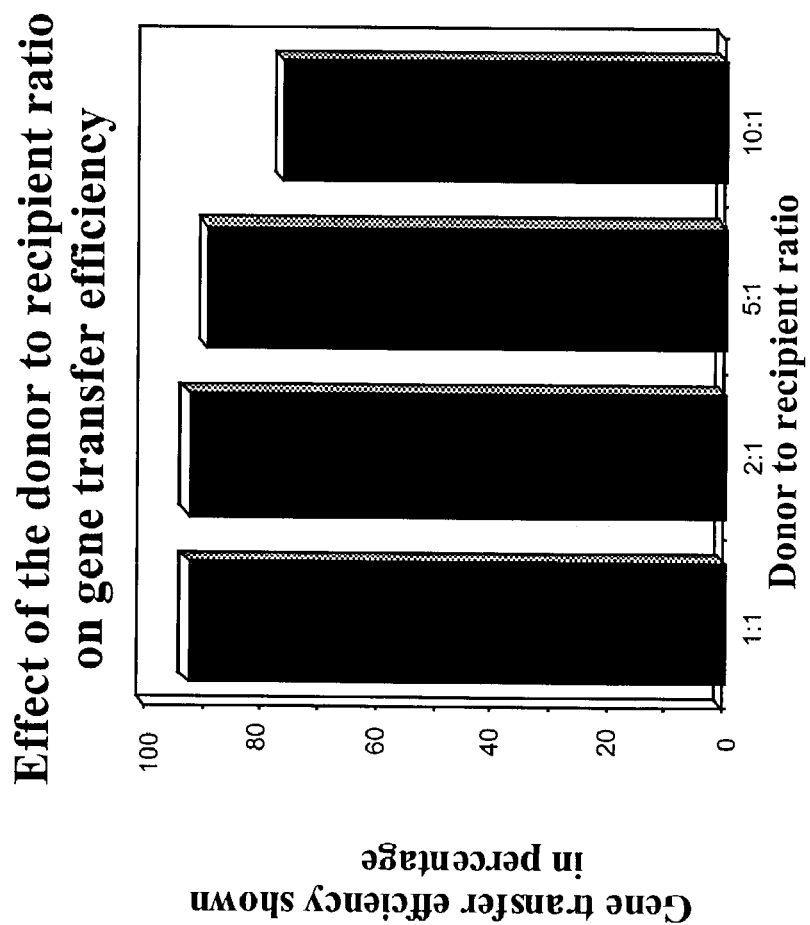
FIG. 14 demonstrates the effect of the donor to recipient ratio on gene transfer efficiency.

The effect of the length of the homology region on gene transfer efficiency was studied, wherein counter-selection against pheS was utilized, and the results are demonstrated in FIG. 13. Greater than 90% efficiency was observed with only 30 bp, although the efficiency could be increased with longer regions. FIG. 14 demonstrates the effect of the donor to recipient ratio on gene transfer efficiency and determined 1:1 or 2:1 donor to recipient ratio was optimal. In FIG. 14, the experiments were performed without counter-selection against pheS.

Figure 15:
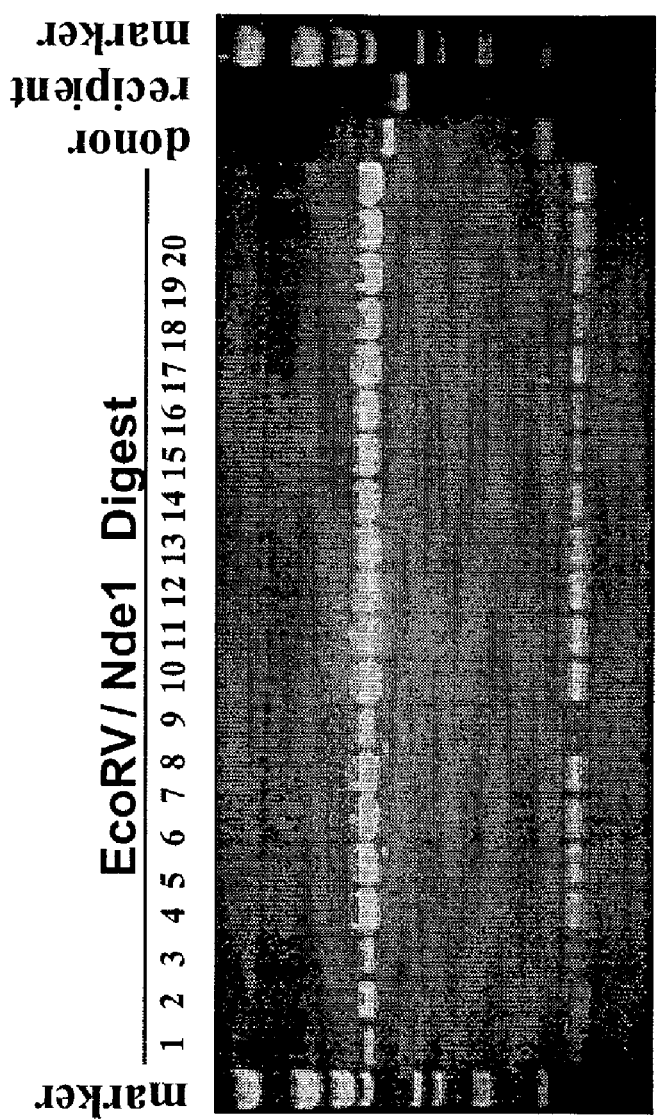
FIG. 15 shows restriction digest of the gene transfer products without counterselection against pheS.

FIG. 15 shows restriction digest of the gene transfer products without counterselection against pheS. Twenty out of twenty have the correct restriction map for a precise transfer into the recipient vector. Overall, without counterselection, the efficiency is approximately 93%.

Figure 16:
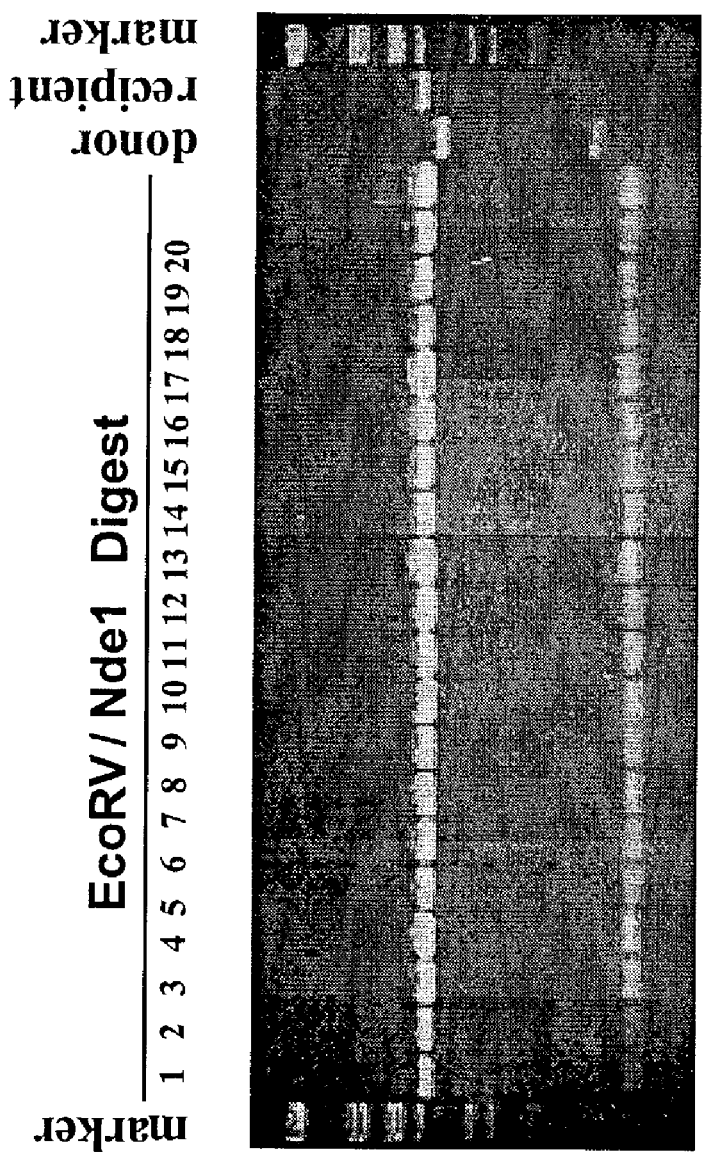
FIG. 16 illustrates restriction digest of the gene transfer products with counterselection of the pheS marker on the recipient vector.

FIG. 16 illustrates restriction digest of the gene transfer products with counterselection of the pheS marker on the recipient vector. Twenty out of twenty have the correct restriction map for a precise transfer into the recipient vector. Overall, with counterselection, the efficiency is approximately 99.8%.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PATENTS

U.S. Pat. No. 4,683,202
U.S. Pat. No. 5,851,808
U.S. Pat. No. 5,925,565
U.S. Pat. No. 5,928,906
U.S. Pat. No. 5,935,819
U.S. Pat. No. 6,277,608
U.S. Pat. No. 6,376,192

PUBLICATIONS

Abremski et al. (1983) Cell 32:1301
Ayres et al. (1993) J. Mol. Biol. 230:174
Babineau et al (1985) J. Biol. Chem. 260:12313;
Boshart, M. et al., Cell 41:521 (1985)
Cox (1983) Proc. Natl. Acad. Sci. USA 80:4223
Dijkema, R. et al., EMBO J. 4:761 (1985)
Fiers et al. (1978) Nature 273:113
Flanagan et al. (1989) J. Mol. Biol. 206:295
Francia and Lobo (1996) J. Bact. 178:894
Fujisawa et al. (1986) EMBO J. 5:713-718
Galsgow et al. (1989) J. Biol. Chem. 264:10072
Gorman, C. M. et al., Proc. Natl. Acad. Sci. USA 79:6777 (1982)
Grindley and Kelley (1976) Mol. Gen. Genet. 143:311
Gronostajski and Sadowski (1985) J. Biol. Chem. 260: 12328
Hoess et al. (1982) Proc. Natl. Acad. Sci. USA 79:3398
Hoess et al. (1984) Proc. Natl. Acad. Sci. USA 81:1026.
Hoess and Abremski (1985) J. Mol. Biol. 181:351
Kim, D. W. et al., Gene 91:217 (1990)
Leslie and Sherratt (1995) EMBO J. 14:1561
Levesque (1990) J. Bacteriol. 172:3745
Lie Q, Li, M Z, Leibman D, Cortez D, and Elledge S J. Current Biology 8:1300-1309 (1998).
Lu and Churchward (1994) EMBO J. 13:1541
Malynn et al. Cell (1988) 54:453
Maniatis T. et al., Science 236:1237 (1987)
Mendiola and de la Cruz (1989) Mol. Microbiol. 3:979
Metcalf et al. (1996) Plasmid 35:1
Metzger et al. (1988) Nature 334:31-36
Meyer-Lean et al. (1987) Nucleic Acids Res. 15:6469
Mizushima, S. and Nagata, S., Nuc. Acids. Res., 18:5322 (1990)
Ohtani et al. (1987) EMBO J. 6:389-395
Pal et al. (1986) J. Mol. Biol. 192:275
Sato et al. J. Bacteriol. 172:1092
Schneider S, Georgiev O, Buchert M, Adams M T, Moelling K, Hovens C M. Gene. 1997 Sep. 15;197 (1-2):337-41.
Seed (1987) Nature 329:840-41
Stark et al. (1989) Cell 58:779
Stenzel et al. (1987) Cell 49:709
Sternberg et al., 1981; Cold Spring Harbor Symp. Quant. Biol. 45:297
Sugiura et al., 1992) J. Bacteriol. 175: 5993
Takebe et al. (1988) Mol. Cell. Biol. 8:466-472
Uetsuki, T. et al., J. Biol. Chem., 264:5791 (1989)
Voss, S. D. et al., Trends Biochem. Sci., 11:287 (1986)
Weisberg et al. In: Lambda II, supra, pp. 211-250
Zhang P, Li M Z, and Elledge S J. Towards genetic genome projects: genomic library screening and gene-targeting vector construction in a single step. Nature Genetics 30: 31-39 (2002).

One skilled in the art readily appreciates that the present invention is well adapted to carry out the objectives and obtain the ends and advantages mentioned as well as those inherent therein. Sequences, strains, mutations, complexes, methods, treatments, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of DNA transfer in vivo, comprising the steps of:
   conjugating a first bacteria having a donor vector comprising a polynucleotide of interest with a second bacteria having a recipient vector, wherein the conjugation results in transfer of the donor vector to the second bacteria; and
   inserting the polynucleotide of interest from the donor vector into the recipient vector by homologous recombination;
   wherein the donor vector is further defined as comprising:
      a polynucleotide of interest;
      a first homology region; and
      a second homology region, and wherein the recipient vector is further defined as comprising:
      a first homology region; and
      a second homology region;
   wherein the homologous recombination is further defined as homologously recombining said polynucleotide of interest into said vector at said homology regions, wherein a double strand break is generated in the recipient vector by restriction enzyme digestion, wherein said restriction enzyme is inducibly expressed in said second bacteria.

2. The method of claim 1, wherein a regulatory sequence for the inducible expression is an arabinose promoter, a galactose promoter, a lactose promoter, a tac promoter, or a rhamnose promoter.

3. The method of claim 1, wherein the restriction enzyme is a meganuclease.

4. The method of claim 3, wherein the meganuclease is I-CeuI, PI-PspI, I-SceI, or PI-SceI.

5. The method of claim 4, wherein the meganuclease is I-SceI.

6. The method of claim 1, wherein the double strand break is generated by HO endonuclease.

7. The method of claim 1, wherein the first homology region, the second homology region, or both homology regions are at least about 10 bp in length.

8. The method of claim 1, wherein the first homology region, the second homology region, or both homology regions are at least about 20 bp in length.

9. The method of claim 1, wherein the first homology region, the second homology region, or both homology regions are at least about 30 bp in length.

10. The method of claim 1, wherein the first homology region, the second homology region, or both homology regions are from about 30 bp to about 60 bp in length.

11. The method of claim 1, wherein the first homology region, the second homology region, or both homology regions are about 50 bp in length.

12. The method of claim 1, wherein the first homology region, the second homology region, or both homology regions are greater than about 60 bp in length.

13. The method of claim 1, wherein the first bacteria is further defined as comprising a conjugative plasmid and the donor vector is further defined as comprising:
   1) a cassette comprising in an operably linked manner and in a 5' to 3' direction:
      a) a first rare restriction enzyme cutting site;
      b) a first homology region;
      c) a polynucleotide of interest;
      d) a second homology region; and
      e) a second rare restriction enzyme cutting site;
   2) a first origin of replication; and
   3) a first selection marker;
   and wherein said second bacteria comprises:
   recombination means and a conditionally regulatable polynucleotide encoding said rare restriction enzyme, and wherein the recipient vector is further defined as comprising:
   1) a cassette comprising in an operably linked manner and in a 5' to 3' direction:
      a) a first homology region;
      b) a first rare restriction enzyme cutting site;
      c) a second rare restriction enzyme cutting site; and
      d) a second homology region;
   2) a second selection marker; and
   3) a second origin of replication.

14. The method of claim 13, wherein the first rare restriction enzyme cutting site and the second rare restriction enzyme cutting site are identical.

15. The method of claim 13, wherein the recipient vector comprises a conditionally lethal gene between said first and second rare restriction enzyme cutting sites.

16. The method of claim 15, wherein the conditionally lethal gene is pheS, sacB, pyrF, or the tetracycline resistance gene.

17. The method of claim 13, wherein the restriction enzyme liberates the polynucleotide of interest from said donor vector and liberates the conditionally lethal gene from the recipient vector prior to homologous recombination of the polynucleotide of interest into the recipient vector at the first and second homology regions and wherein, following the recombination, the recipient vector no longer comprises the rare restriction enzyme cutting site.

18. The method of claim 17, wherein the loss of the rare restriction enzyme cutting site on the recipient vector following the homologous recombination is utilized as a means to select against bacteria wherein the homologous recombination did not occur.

19. The method of claim 13, wherein said method further comprises selection for the second bacteria following a recombining step through the second selection marker.

20. The method of claim 15, wherein the product encoded by the conditionally lethal gene selects against a bacteria wherein the homologous recombination did not occur.

21. The method of claim 13, wherein the conjugative plasmid is an F' plasmid, an RP4 plasmid, or an R388 plasmid.

22. The method of claim 21, wherein the F' plasmid is F' (lac$^+$pro$^+$ΔoriT::Tc).

23. The method of claim 13, wherein the first or second selection marker is an antibiotic resistance marker or a nutritional marker.

24. The method of claim 23, wherein the antibiotic resistance is to kanamycin, ampicillin, tetracycline, chloramphenicol, spectinomycin, gentamycin, zeomycin, or streptomycin.

25. The method of claim 23, wherein the nutritional marker is trpA, trpB, proA, hisA, or hisB.

26. The method of claim 13, wherein the first origin of replication is R6Kγ and the first bacteria comprises the pir-116 gene or the pirl gene.

27. The method of claim 13, wherein the polynucleotide of interest is linked to a drug resistance marker within the first and second homology regions.

28. The method of claim 1, wherein the first and second bacteria are gram-negative bacteria.

29. The method of claim 1, wherein the first bacteria has the genotype F' pir 116.

30. The method of claim 1, wherein the second bacteria has the genotype umuC::P$^{BAD}$-I-SceI.

* * * * *